US008206464B2

(12) United States Patent
Cremer et al.

(10) Patent No.: US 8,206,464 B2
(45) Date of Patent: Jun. 26, 2012

(54) BLUE POLYMERIC HAIR DYES

(75) Inventors: Christian Cremer, Lörrach (DE); Sophie Marquais-Bienewald, Hegenheim (FR); Olof Wallquist, Bottmingen (CH); Beate Fröhling, Grenzach-Wyhlen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/812,781

(22) PCT Filed: Jan. 7, 2009

(86) PCT No.: PCT/EP2009/050096
§ 371 (c)(1),
(2), (4) Date: Dec. 1, 2010

(87) PCT Pub. No.: WO2009/090124
PCT Pub. Date: Jul. 23, 2009

(65) Prior Publication Data
US 2011/0061179 A1    Mar. 17, 2011

(30) Foreign Application Priority Data

Jan. 17, 2008    (EP) ..................................... 08150362

(51) Int. Cl.
*A61Q 5/10*    (2006.01)
*C07D 213/22*    (2006.01)
(52) U.S. Cl. ............. 8/405; 8/552; 8/554; 8/647; 8/657; 546/264
(58) Field of Classification Search ............... 8/405, 552, 8/647, 657; 546/264
See application file for complete search history.

(56) References Cited

U.S. PATENT DOCUMENTS

| | | | |
|---|---|---|---|
| 3,567,678 A | 3/1971 | Kalopissis | |
| 4,182,612 A | 1/1980 | Sokol | |
| 5,891,199 A | 4/1999 | Wachter | |
| 6,306,182 B1 | 10/2001 | Chan | |
| 7,731,761 B2 * | 6/2010 | Marquais-Bienewald et al. ................. | 8/405 |

FOREIGN PATENT DOCUMENTS

| | | |
|---|---|---|
| DE | 1492063 A1 | 10/1969 |
| DE | 19510312 A1 | 9/1996 |
| WO | 95/01772 A | 1/1995 |
| WO | 2006/134051 A | 12/2006 |
| WO | 2008/009579 A | 1/2008 |
| WO | WO 2008/009579 A1 * | 1/2008 |

OTHER PUBLICATIONS

Copending U.S. Appl. No. 12/812,778, filed Jul. 14, 2010.
Copending U.S. Appl. No. 12/812,785, filed Jul. 14, 2010.
Copending U.S. Appl. No. 12/812,782, filed Jul. 14, 2010.

* cited by examiner

*Primary Examiner* — Eisa Elhilo
(74) *Attorney, Agent, or Firm* — Sheila A. Loggins

(57) ABSTRACT

Disclosed are cationic polymeric dye with a hue value of h=210° to 330° comprising: a) a polymer backbone, b) a residue of an organic dye, and c) optionally colorless organic groups, wherein (b) and (c) are covalently bound to the polymer backbone (a), and wherein the cationic charges can independently be part of the dye or the colorless organic groups. The dyes are distinguished by their depth of shade and their good fastness properties to washing, such as, for example, fastness to light, shampooing and rubbing.

22 Claims, No Drawings

BLUE POLYMERIC HAIR DYES

The present invention relates to novel polymeric dyes and compositions comprising these compounds, to a process for their preparation and to their use for dyeing of organic materials, such as keratin-containing fibers, wool, leather, silk, cellulose or polyamides.

It is well known that cationic compounds have a good affinity to negative charged hair. These characteristics have been used to contact the hair with small molecules, but also with polymers.

Therefore, the present invention relates to cationic polymeric dye with a hue value of h=210° to 330° comprising
(a) a polymer backbone,
(b) a residue of an organic dye and
(c) optionally colorless organic groups,
wherein (b) and (c) are covalently bound to the polymer backbone (a), and wherein the cationic charges can independently be part of the dye or the colorless organic groups.

"Hue" is the correct word to use to refer to just the pure spectrum colors. Hue is the most obvious characteristic of a color. There is really an infinite number of possible hues. A full range of hues exists, for example, between red and yellow. In the middle of that range are all the orange hues. Similarly, there is a range of hues between any other hues.

"Value" is defined as the relative lightness or darkness of a color. Contrast of value separates objects in space, while gradation of value suggests mass and contour of a contiguous surface.

Any given color can be described in terms of its value and hue. In addition, the various physical phenomena and psychological effects combine to affect our perceptions of a color.

Colors shades are defined according to the CIE "Commission Internationale de l'Eclairage" by the CIE L*a*b* or alternatively by the CIEL*C*h* system, where L*, C* and h* are respectively the lightness, the chroma and the hue value; a* and b* respectively the red-green and yellow-blue axis. The hue angle defines the actual shade: angle of 0° C.=red, 90° C.=yellow, 180° C.=green, 270° C.=blue.

Preferably the residues of the organic dyes (b) are selected from the group of anthraquinone, azo, triphenylmethane, dioxazine, indigoid, indophenol, naphthalimide, naphthoquinone, naphthoquinone imine, benzindolium, quinolinium imine, oxazine, phthalocyanine, phenazine and thiazine dyes.

Most preferably the residues of the organic dyes (b) are selected from the group of anthraquinone and azo dyes.

Most preferably the polymeric dyes are selected from the group of 1,4-diamino-anthraquinone, thiazolazo, benzothiazolazo, thiadiazolazo and imidazolazo dyes.

Preferred are polymeric dyes, wherein 1 to 3 different residues of an organic dye (b) are bound to the polymer backbone (a).

The polymer backbone (a) is preferably selected from polyethyleneimine, polypropyleneimine, polyvinylamine; polyvinylimine; polysiloxane; polystyrene, polyvinylimidazol, polyvinylpyridine, poly-DADMAC, polyvinylalcohol, polyacrylate, polymethacrylate; polyguanidines, polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polysaccharide, starch, cellulose, lignin; and copolymers and blends of the mentioned polymers.

Most preferred polymeric dyes according to the present invention correspond to the formula

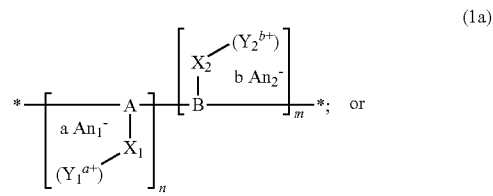

(1a)

or

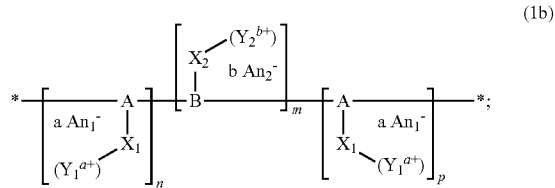

(1b)

wherein
A and B, independently from each other represent a polymer backbone (a);
$X_1$ and $X_2$, independently from each other are a linkage group selected from —$C_1$-$C_{30}$alkylene-, —$C_2$-$C_{12}$alkenylene-, —$C_5$-$C_{10}$arylene, —$C_5$-$C_{10}$cycloalkylene or —$C_1$-$C_{10}$alkylene($C_5$-$C_{10}$arylene) which may be interrupted and/or terminated at one or both ends by one or more than one —O—, —S—, —N=, —N($R_1$)—, S(O)—, —$SO_2$—, —($CH_2CH_2$—O$)_{1-5}$—, —($CH_2CH_2CH_2$—O$)_{1-5}$—, —C(O)—, —C(O)O—, —OC(O)—,

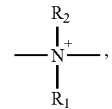

—CON($R_1$)—, —C(N$R_1R_2)_2$—, —($R_1$)NC(O)—, —C(S)$R_1$— or an optionally substituted, saturated or unsaturated, fused or non-fused aromatic or nonaromatic (hetero)cyclic bivalent radical optionally comprising at least one heteroatom; —O—; —S—; —N($R_1$)—; —S(O)—; $SO_2$—; —($CH_2CH_2$—O$)_{1-5}$—; —C(O)—; —C(O)O—, —OC(O)—;

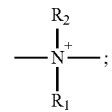

—C(O)N($R_1$)—; S(O$)_2$N($R_1$)—; —C(N$R_1R_2)_2$—; —($R_1$)NC(O)—; —C(S)$R_1$—; saturated or unsaturated, fused or non-fused aromatic or nonaromatic bivalent radical optionally comprising at least one heteroatom, which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), halogen, hydroxy; or the direct bond;
$R_1$ and $R_2$ independently from each other hydrogen; unsubstituted or substituted, straight-chain or branched, monocyclic or polycyclic, interrupted or uninterrupted $C_1$-$C_{14}$alkyl; $C_1$-$C_{14}$ hydroxyalkyl; $C_1$-$C_{14}$ aminoalkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$Y_1$ and $Y_2$ independently from each other are a residue of an organic dye (b), hydrogen, halogen or $C_1$-$C_5$alkyl; $C_1$-$C_5$alkoxy; $C_1$-$C_5$alkylamino; $C_6$-$C_{10}$aryloxy; $C_6$-$C_{10}$arylamino; $SO_2R_1$; wherein at least one of $Y_1$ and $Y_2$ is a residue of an organic dye;

$An_1$ and $An_2$ independently from each other are an anion;

a and b independently from each other are a number from 1 to 3;

m is a number from 0 to 5000;

n is a number from 0 to 5000; and p is a number from 1 to 5000;

wherein the sum of $m+n+p \leqq 3$.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl, tridecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{30}$alkylene is for example methylene, ethylene, propylene, isopropylene, n-tetramethylene, sec-tetramethylene, tert-tetramethylene, n-pentamethylene, 2-pentamethylene 3-pentamethylene, 2,2'-dimethylpropylene, cyclopentamethylene, cyclohexamethylene, n-hexamethylene, n-octamethylene, 1,1',3,3'-tetramethyltetramethylene, 2-ethylhexamethylene, nonamethylene, decamethylene, tridecamethylene, tetradecamethylene, pentadecamethylene, hexadecamethylene, heptadecamethylene, octadecamethylene, nonadecamethylene or eicosamethylene.

Preferably, $X_1$ and $X_2$, independently from each other are a bivalent radical of formula (2a) -$(T)_t(Z)_z$—, wherein T is a radical selected from saturated or unsaturated, linear or branched —$C_1$-$C_{12}$alkylene, —C(O)—, —(CH$_2$CH$_2$—O)$_{1-5}$—, —(CH$_2$CH$_2$CH$_2$—O)$_{1-5}$—, —C(O)O—, —OC(O)—, —N(R$_1$)—, —CON(R$_1$)—, —(R$_1$)NC(O)—, —O—, —S—, —S(O)—, —S(O)$_2$—, —S(O)$_2$—N(R$_1$)—, and —N$^+$(R$_1$)(R$_2$)—, which may be interrupted and/or terminated at one or both ends by one or more than one —O—, —S—, —SO$_2$—, —N(R$_5$)—, —C(O)—,

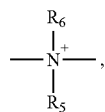

—CON(R$_5$)—, —(R$_5$)NC(O)— and which is optionally substituted by $C_1$-$C_6$alkyl, $C_1$-$C_6$alkoxy, $C_6$aryl, halogen, hydroxy or Y$^+$; or is a direct bond;

Z is —(CH$_2$)$_2$SO$_2$—; —CH$_2$CHRCO—NR$_1$—; or a biradical of formula

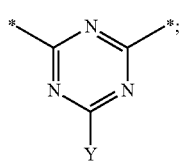

(3a)

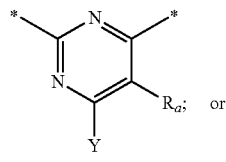

(3b)

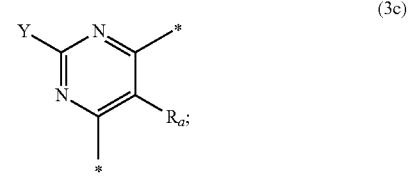

(3c)

$R_1$ and $R_2$ independently from each other are hydrogen; $C_1$-$C_6$alkyl; $C_1$-$C_6$alkoxy; $C_1$-$C_6$alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$-aryloxy; $C_6$-$C_{10}$-arylamino; $SO_2R_1$; chlorine; or fluorine;

Y is $R_a$; $Y_1^{a+}$; or $Y_2^{b+}$;

$Y_1^{a+}$ and $Y_2^{b+}$ are halogen; hydrogen; CH$_3$; or a residue of an organic dye selected from anthraquinone, azo, azomethine, hydrazomethine, merocyanine, methane, naphthoquinoneimine, naphthalimide and styryl dyes, wherein at least one of the $Y_1^{a+}$ and $Y_2^{b+}$ is a residue of an organic dye; and a and b independently from each other are 1, 2 or 3.

More preferably

T is selected from —O$_2$—$C_3$alkylene-; —C(O)—; —C(O)—CH$_2$—; and —S(O)$_2$—$C_{2-6}$alkylene-;

Z is hydrogen or $C_1$-$C_6$ alkyl; or a biradical of formula

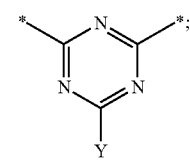
(3a)

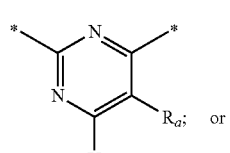
(3b)

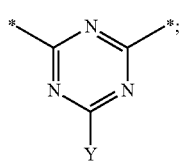
(3c)

$R_1$ and $R_2$ independently from each other are hydrogen; $C_1$-$C_3$alkyl; $C_1$-$C_4$-alkoxy; $C_1$-$C_4$-alkylamino; $C_6$-aryloxy; or $C_6$-arylamino;

$R_a$ is chlorine, fluorine, methyl or SO$_2$CH$_3$;

$Y_1^{a+}$ and $Y_2^{b+}$ are hydrogen; halogen; CH$_3$; or a residue of an organic dye selected from 1,4-diaminosubstituted anthraquinone, thiazolazo, benzothiazolazo, thiadiazolazo, imidazolazo and naphthalimide dyes, wherein at least one of the $Y_1^{a+}$ and $Y_2^{b+}$ is a residue of an organic dye;

t and z, independently from each other are 0 or 1 with the proviso that at least one of t or z is 1.

Preferably in formulae (1a) and (1b)

A and B, independently from each other are selected from polymers of monoolefins and diolefins; mixtures of polymers of monoolefins and diolefins; copolymers of monoolefins and diolefins with each other or with other vinyl monomers; polystyrene, poly(p-methylstyrene), poly(α-methylstyrene); aromatic homopolymers and copolymers derived from vinyl aromatic monomers; copolymers and hydrogenated copolymers of vinyl aromatic monomers and comonomers selected from ethylene, propylene, dienes, nitriles, acids, maleic anhydrides, maleimides, vinyl acetate and vinyl chloride or acrylic derivatives and mixtures thereof; graft copolymers of vinyl aromatic monomers; halogen-containing polymers; polymers derived from α,β-unsaturated acids and derivatives thereof; copolymers derived from α,β-unsaturated acids and derivatives thereof with other unsaturated monomers; polymers derived from unsaturated alcohols and amines or the acyl derivatives or acetals thereof; homopolymers and copolymers of cyclic ethers; polyacetals; polyphenylene oxides and sulfides, and mixtures of polyphenylene oxides with styrene polymers or polyamides; Polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polyguanidines, polyureas, polyimides, polyamide-imides, polyetherimides, polyetherimides, polyhydantoins and polybenzimidazoles; polyesters derived from dicarboxylic acids and diols and/or from hydroxycarboxylic acids or the corresponding lactones; polycarbonates and polyester carbonates; polyketones; polysulfones, polyether sulfones and polyether ketones; Crosslinked polymers derived from aldehydes on the one hand and phenols, ureas and melamines on the other hand; polysiloxanes; natural polymers; and blends of the mentioned polymers.

Examples for polymers of monoolefins and diolefins are polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerization (normally under high pressure and at elevated temperature).

b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Mixtures of the polymers mentioned above are for example mixtures of polypropylene with polyisobutylene, polypropylene with polyethylene (for example PP/HDPE, PP/LDPE) and mixtures of different types of polyethylene (for example LDPE/HDPE).

Examples of copolymers of monoolefins and diolefins with each other or with other vinyl monomers are ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Homopolymers and copolymers mentioned above may have any stereostructure including syndiotactic, isotactic, hemi-isotactic or atactic; where atactic polymers are preferred. Stereoblock polymers are also included.

Examples of aromatic homopolymers and copolymers derived from vinyl aromatic monomers including styrene are α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

Examples for copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof are for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

Hydrogenated aromatic polymers derived from hydrogenation of polymers mentioned above especially including polycyclohexylethylene (PCHE) prepared by hydrogenating atactic polystyrene, often referred to as polyvinylcyclohexane (PVCH).

Homopolymers and copolymers may have any stereostructure including syndiotactic, isotactic, hemi-isotactic or atactic; where atactic polymers are preferred. Stereoblock polymers are also included.

Examples for graft copolymers of vinyl aromatic monomers are styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

Examples for halogen-containing polymers are polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

Examples for polymers derived from α,β-unsaturated acids and derivatives thereof are polyacrylates and polymethacrylates; polymethyl methacrylates, polyacrylamides and polyacrylonitriles, impact-modified with butyl acrylate.

Examples for copolymers of the monomers mentioned above with each other or with other unsaturated monomers are acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

Examples for polymers derived from unsaturated alcohols and amines or the acyl derivatives or acetals thereof are for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in above.

Examples for homopolymers and copolymers of cyclic ethers are polyalkylene glycols, polyethylene oxide, polypropylene oxide or copolymers thereof with bisglycidyl ethers.

Examples for polyacetals are polyoxymethylene and those polyoxymethylenes which contain ethylene oxide as a comonomer; polyacetals modified with thermoplastic polyurethanes, acrylates or MBS.

Examples for polyamides and copolyamides derived from diamines and dicarboxylic acids and/or from aminocarboxylic acids or the corresponding lactams are polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Examples for polyesters derived from dicarboxylic acids and diols and/or from hydroxycarboxylic acids or the corresponding lactones are polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

Examples for crosslinked polymers derived from aldehydes on the one hand and phenols, ureas and melamines on the other hand are phenol/formaldehyde resins, urea/formaldehyde resins and melamine/formaldehyde resins.

Examples for natural polymers are cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

Example for blends of the aforementioned polymers (polyblends) are PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

In formulas (1a) and (1b) both the polymer backbone (A and B) and residue of an organic dye ($Y_1$ and $Y_2$) preferably have a functional group selected from the electrophilic group selected from halide, tosylate, mesylate, methoxy, acid chloride, sulfonyl chloride, epoxides, anhydride; or a nucleophilic group selected from amine, hydroxyl and thiol.

The molecular weight of the polymeric dye is preferably from 400 to 500000.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

More preferably the polymer is a polyethyleneimine with a average molecular weight from 400-1800 g/mol, preferably from 400-1000 g/mol and the organic dye is bound via the primary secondary or tertiary amines of the polyethyleneimine.

Most preferably the polymer is a homopolymer or a copolymer of 4-vinylpyridine or 2-vinylpyridine or vinylimidazole.

Most preferred dyes correspond to the formula

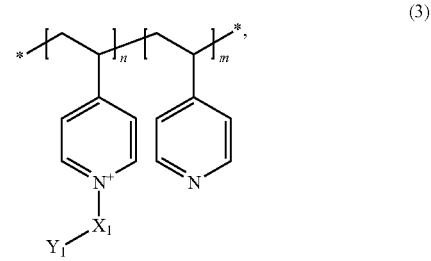

(3)

wherein
the poly-4-vinylpyridine has an average molecular weight of MW=1000 and 500000 g/mol,
$Y_1$ is a residue of an organic dye (b) selected from anthraquinone, and azo dyes,
$X_1$ is defined as in formula (2a); and
the ratio of n:m is between 1:10 and 10:1.
Preferred are also dyes of formula

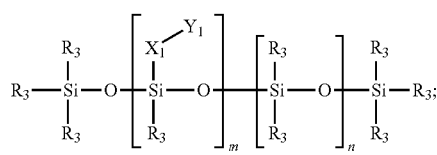

(5)

wherein
$R_3$ is $C_1$-$C_5$alkyl; and
$X_1, X_2, Y_1, Y_2$, m and n are defined as in formula (1a) and (1b).
Preferred are also polymeric dyes of formula

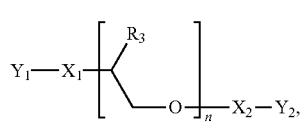

(7)

wherein
$R_3$ is $C_1$-$C_5$alkyl; and
$X_1, X_2, Y_1, Y_2$ and n are defined as in formula (1a) and (1b)

The polymeric dyes according to the present invention are prepared by using at least one of the following reactive dye building blocks BB-01
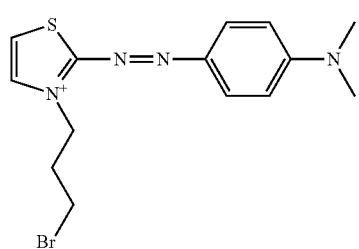

BB-02
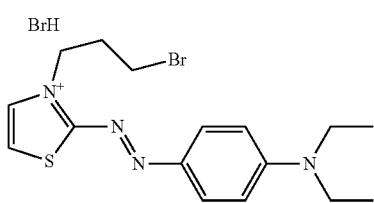

BB-03
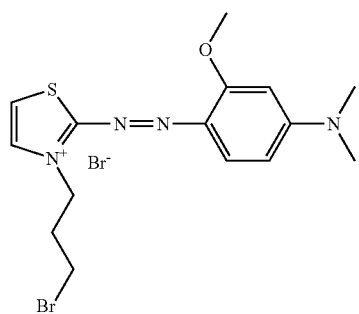

BB-04
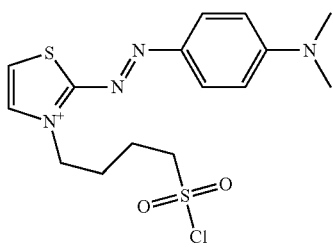

BB-05
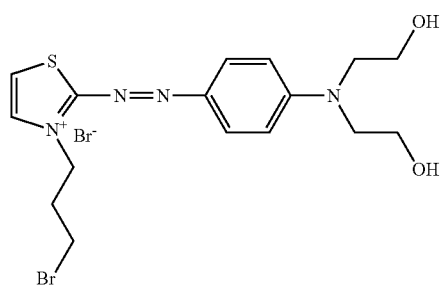

BB-06
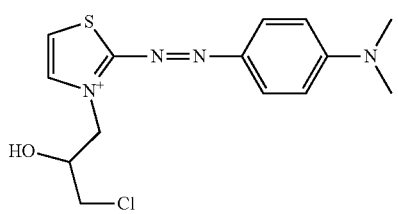

BB-07
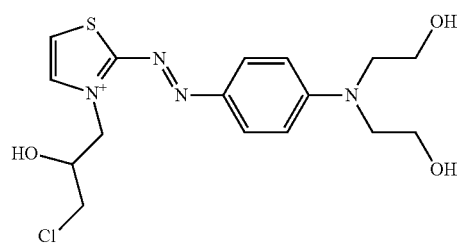

BB-08
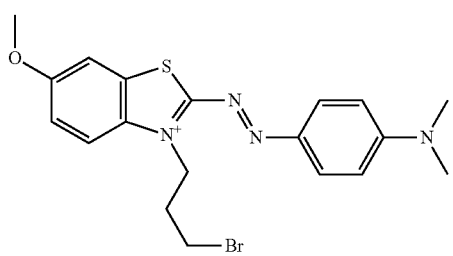

-continued
BB-09
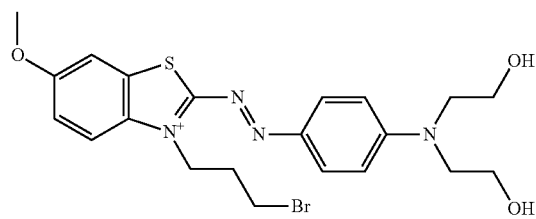
BB-10
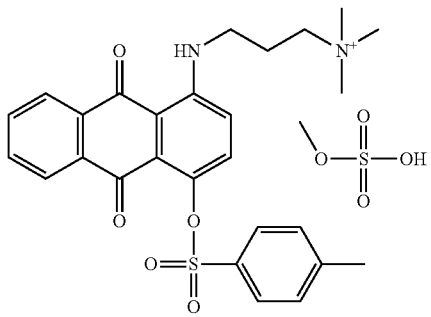
BB-11
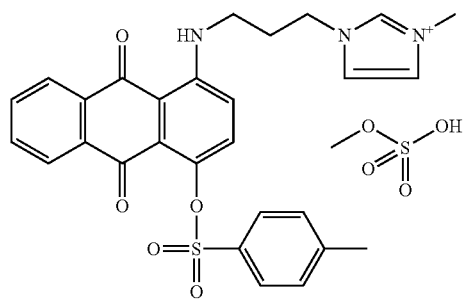
BB-12
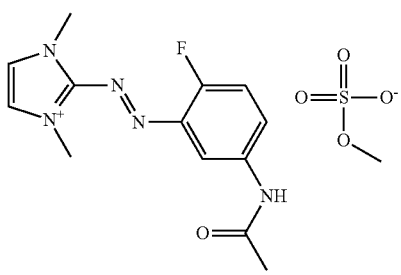
BB-13
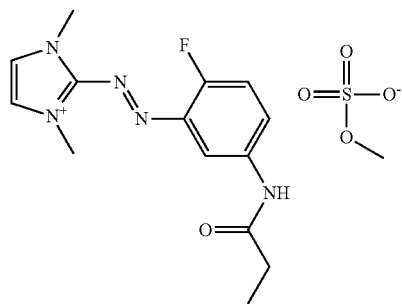
BB-14
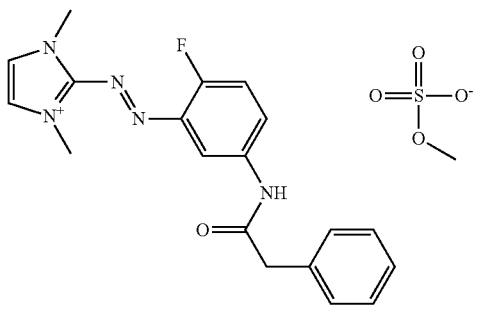
BB-15
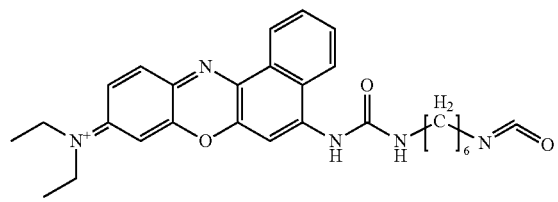
BB-16
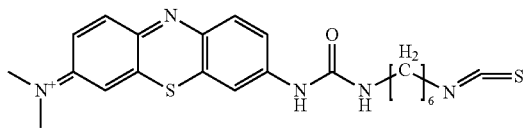
BB-17
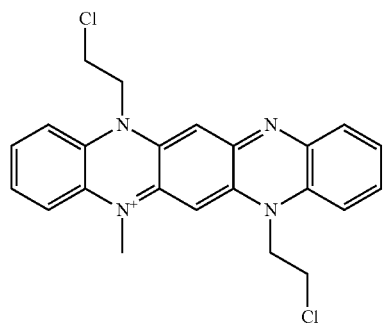
BB-18
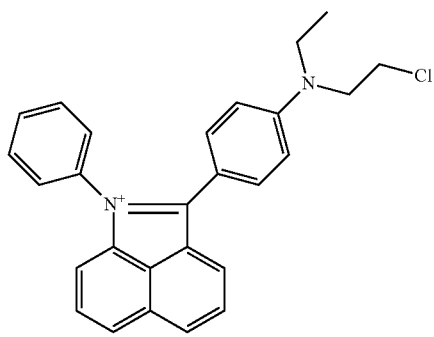

-continued
BB-19
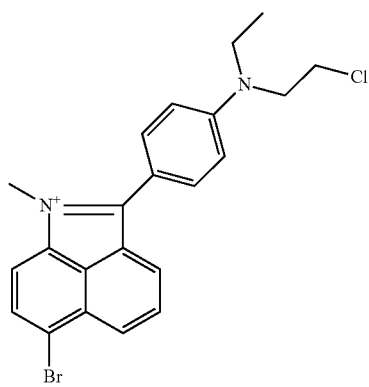
BB-20
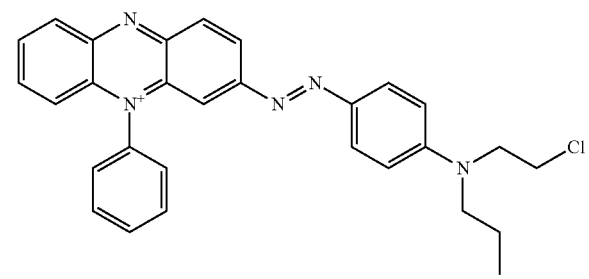
BB-21
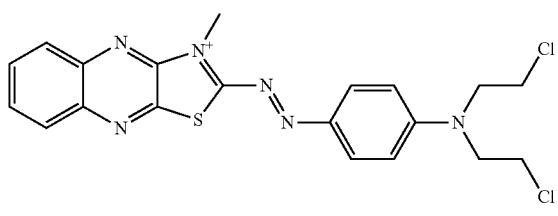
BB-22
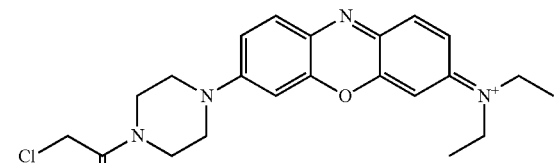
BB-23
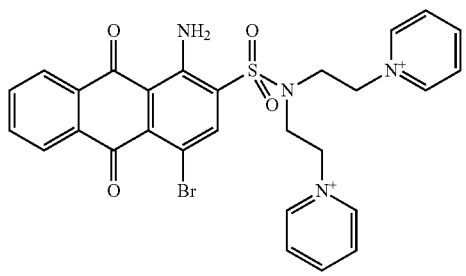
BB-24
BB-25
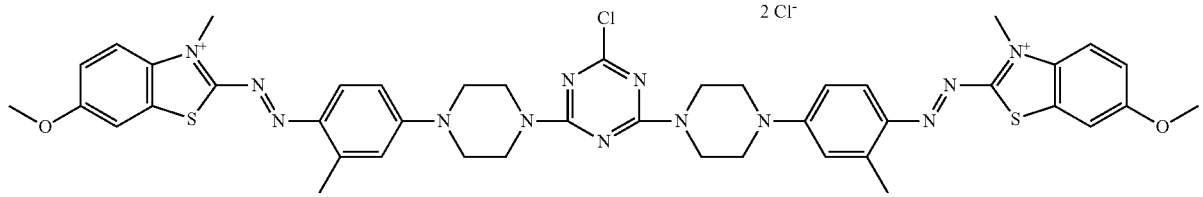
BB-26
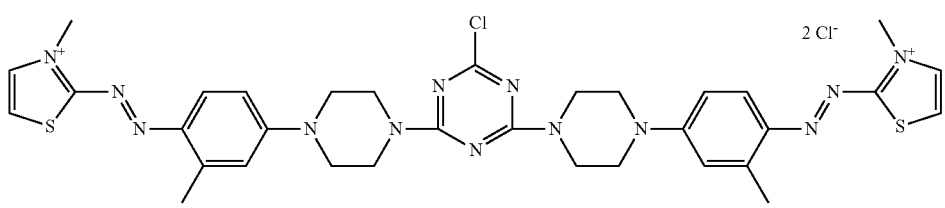

-continued
BB-27
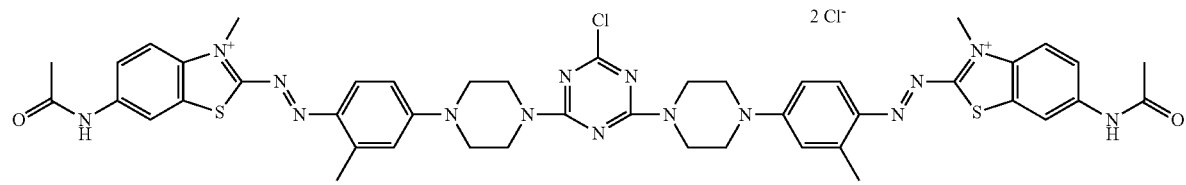
BB-28
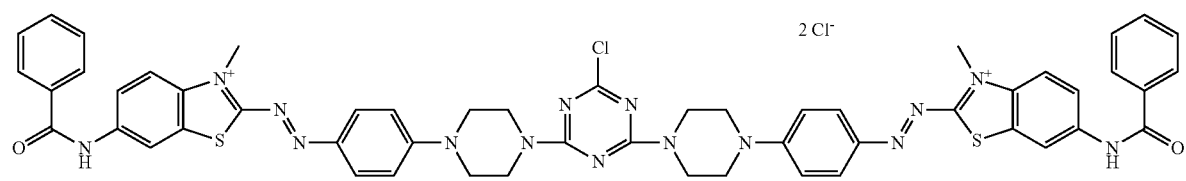
BB-29
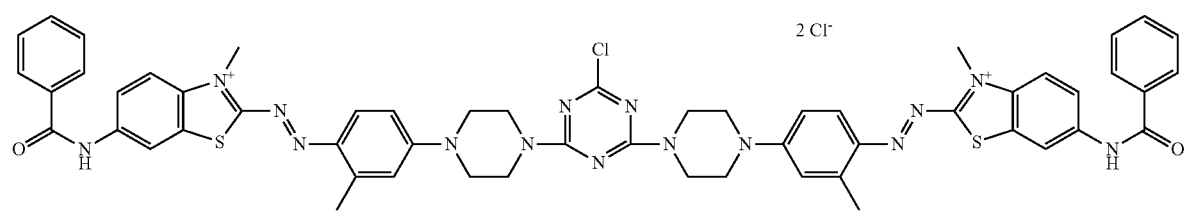
BB-30
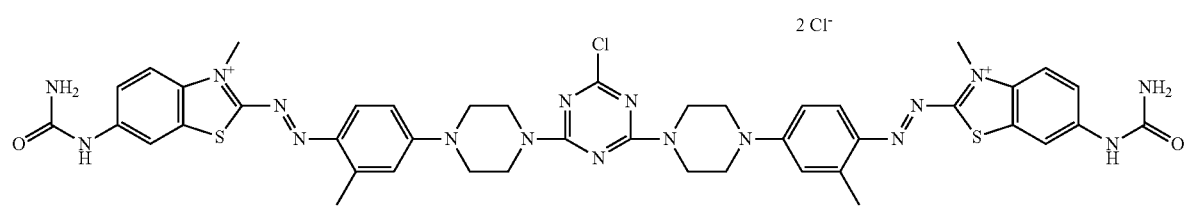
BB-31
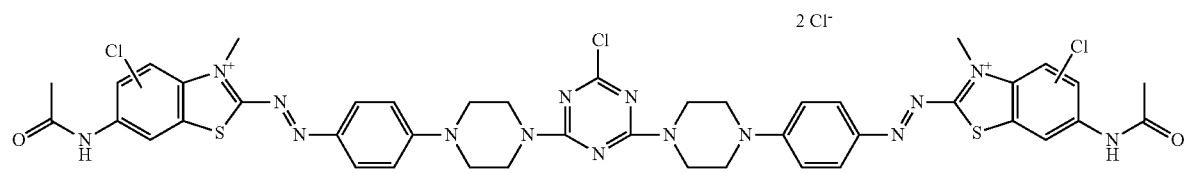
BB-32
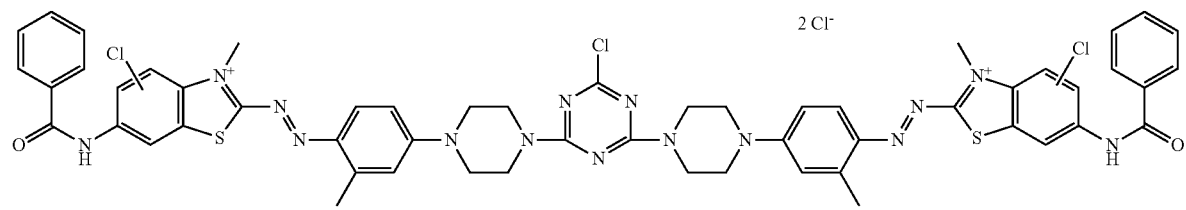

Furthermore the polymeric dyes according to the present invention can be prepared by using at least one dye selected from the following chromophores:

(CP-01)

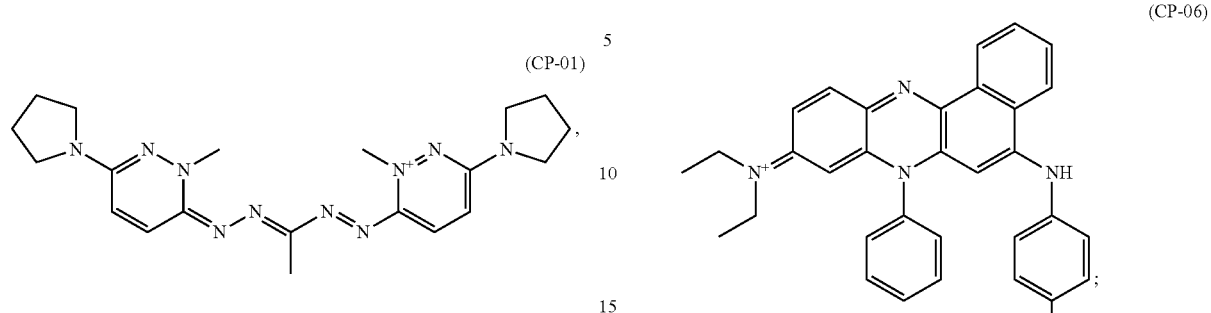

which has been disclosed in EP 1 378 544 (example 10), (CP-02)

which is disclosed in EP1 378 544 (example 10), (CP-03)

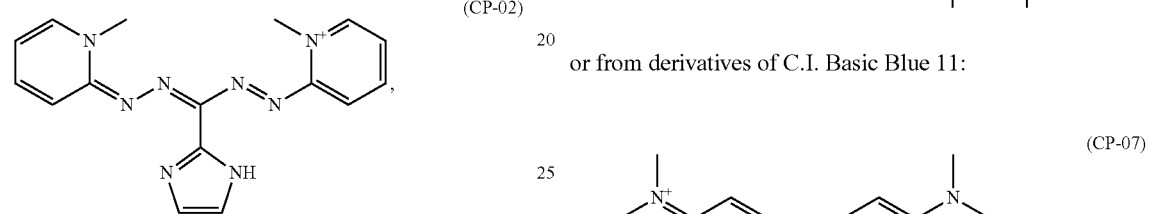

which is disclosed in DE 10139561 (page 13), (CP-04)

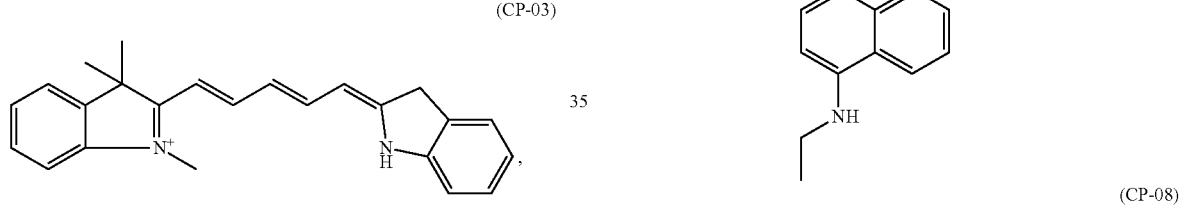

which is disclosed in FR 2 886 842 (formula VI), (CP-05)

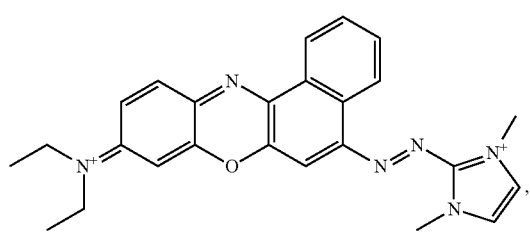

which is disclosed in FR 2 886 842 (formula VII), also from derivatives of C.I. Basic Blue 13:

(CP-06)

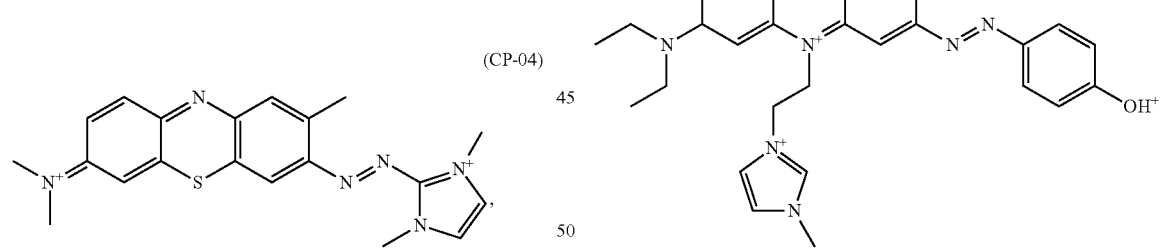

or from derivatives of C.I. Basic Blue 11:

(CP-07)

; or (CP-08)

The dyes of formula (1a) or (1b) according to the invention are suitable for dyeing organic materials, such as keratin-containing fibers, wool, leather, silk, cellulose or polyamides, cotton or nylon, and preferably human hair including body hairs like eyebrows, eyelashes, pubic-, breast-, armpit- and beard hair. Also animal hair can be colored with the inventive hair dyes. The dyeings obtained are distinguished by their depth of shade and their good fastness properties to washing, such as, for example, fastness to light, shampooing and rubbing.

Generally, hair dyeing agents on a synthetic base may be classified into three groups:
 temporary dyeing agents
 semipermanent dyeing agents, and
 permanent dyeing agents.

The multiplicity of shades of the dyes can be increased by combination with other dyes.

Therefore the dyes of formula (1a) and (1b) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1a) and (1b) may be used in combination with at least one single direct dye different from the dyes of formula (1a) and (1b).

The inventive polymeric dyes do not require any addition of an oxidizing agent to develop their dyeing effect. This fact could possibly reduce the damage of the hair. In addition many of the perceived or documented disadvantages of current oxidative hair dyes like their skin irritation, skin sensitization and allergenic properties can be prevented by the use of the inventive hair dyes. Also, the inventive hair dyes are easier to apply and to use in formulations than oxidative hair dyes since no chemical reaction occurs upon application on the head. Especially advantageous is the fact, that the dyeing time is significantly shorter (ca. 5-10 min) than dyeing using oxidative dyes.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, the dyes of formula (1a), (1b) and (1c) may be combined with at least one cationic azo dye, for example the compounds disclosed in GB-A-2 319 776 as well as the oxazine dyes described in DE-A-299 12 327 and mixtures thereof with the other direct dyes mentioned therein.

The dyes of formula (1a) and (1b) may also be combined with acid dyes, for example the dyes which are known from the international names (Color index), or trade names.

The dyes of formula (1a) and (1b) may also be combined with uncharged dyes.

Furthermore, the dyes of formula (1a) and (1b) may also be used in combination with oxidation dye systems.

Furthermore, autooxidizable compounds may be used in combination with the dyes of formula (1a) and (1b).

The dyes of formula (1a) and (1b) may also be used in combination with naturally occurring dyes.

Furthermore, the dyes of formula (1a) and (1b) may also be used in combination with capped diazotized compounds.

Suitable diazotized compounds are for example the compounds of formulae (1)-(4) in WO 2004/019897 (bridging gages 1 and 2) and the corresponding water soluble coupling components (I)-(IV) as disclosed in the same reference on p. 3 to 5.

Furthermore, the dyes of the present invention can also be combined with dyes which are prepared by the reaction of a reactive carbonyl-compound and a CH-acidic compound as described in DE 10 2006 062 435 A1, WO 00038638, DE 10241076 and WO 05120445, with thiadiazol dyes as described in DE 10 2006 036898 and DE 10 2005 055496, with fluorescent stilbenic sulphur dyes as described in for example WO 07110532, WO 07110542, with tetraazapentamethine dyes as described in WO 07071684 and WO 07071686, with dimeric cationic dyes as described in FR 2879195, FR 2879127, FR 2879190, FR 2879196, FR 2879197, FR 2879198, FR 2879199, FR 2879200, FR 2879928, FR 2879929, WO 06063869, with azo and styryl dyes as described in EP 0850636, with polymeric anionic dyes as described in FR 2882929, with disulfide dyes as described in WO 0597051, EP 1647580, WO 06136617, with thiol dyes as described in WO 07025889, WO 07039527, with conductive polymers as described in US 20050050650, U.S. Pat. No. 7,217,295

The present invention also relates to formulations, which are used for the dyeing of organic materials, preferably keratin-containing fibers, and most preferably human hair, comprising at least one dye of formula (1a) and (1b).

Preferably the dyes of formula (1a) and (1b) are incorporated into the composition for treating organic material, preferably for dyeing in amounts of 0.001-5% by weight (hereinafter indicated merely by "%"), particularly 0.005-4%, more particularly 0.1-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, I. 16 to 31.

The pH value of the ready-to-use dyeing compositions is usually from 2 to 11, preferably from 5 to 10.

The dyeing compositions of the present invention are applied on the hair in a temperature range of 10 to 200, preferably 18 to 80, and most preferably from 20 to 40° C.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Suitable cosmetic hair-care formulations are hair-treatment preparations, e.g. hair-washing preparations in the form of shampoos and conditioners, hair-care preparations, e.g. pretreatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, I. 70 to col 3, I. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

If the dyes of formula (1a) and (1b) are used together with oxidation dyes and/or the addition salts thereof with an acid, they may be stored separately or together. Preferably the oxidation dyes and the direct dyes which are not stable to reduction or base are stored separately.

The dyes of formula (1a) and (1b) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilizers.

The following adjuvants are preferably used in the hair dyeing compositions of the present invention: non-ionic polymers, cationic polymers, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers; quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilizers, anti-dandruff active ingredients, substances for adjusting the pH value, panthenol, pantothenic acid, allantoin, pyrrolidonecarboxylic acids and salts thereof, plant extracts and vitamins, cholesterol; light stabilizers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1a) and (1b) and
(b) leaving the fiber to stand and then rinsing the fiber.

The dyes of formula (1a) and (1b) are suitable for all-over dyeing of the hair, that is to say when dyeing the hair on a first occasion, and also for re-dyeing subsequently, or dyeing of locks or parts of the hair.

The dyes of formula (1a) and (1b) are applied on the hair for example by massage with the hand, a comb, a brush, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1a) and (1b), a base and an oxidizing agent.

A preferred embodiment for dyeing keratin-containing fibers, in particular human hair, with a dye of formula (1a) and (1b) and an oxidizing agent, comprises
$a_1$) treating the keratin-containing fiber with the oxidizing agent, which optionally contains at least one dye of formula (1a) and (1b),
$b_1$) treating the keratin-containing fiber with an oxidizing agent free composition, which optionally contains at least one dye of formula (1a) and (1b); or alternatively
$a_2$) treating the keratin-containing fiber with an oxidizing agent free composition, which optionally contains at least one dye of formula (1a) and (1b);
$b_2$) treating the keratin-containing fiber with an oxidizing agent, which optionally contains least one dye of formula (1a) and (1b),
with the proviso that at least in one of the process steps $a_1$), $a_2$), $b_1$) or $b_2$) a dye of formula (1a) and (1b) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1a) and (1b) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1a) and (1b) which are stable to reduction can be stored together with the oxidizing agent free compositions and may be applied as a single composition.

Advantageously the compositions comprising a dye of formula (1a) and (1b) which are not stable to reduction are prepared with the oxidizing agent free composition just before the dyeing process.

In a further embodiment, the dye of formula (1a) and (1b) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromate fixations are also applicable if a shading powder on the basis of semi-permanent, direct hair dyes is used.

Further preferred oxidizing agents are
oxidizing agents to achieve lightened coloration, as described in WO 97/20545, especially p. 9, l. 5 to 9,
oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

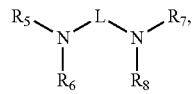

wherein
L is a propylene residue, which may be substituted with OH or $C_1$-$C_4$alkyl; and
$R_5$, $R_6$, $R_7$ and $R_8$ independently or dependently from each other are hydrogen; $C_1$-$C_4$alkyl; or hydroxy-($C_1$-$C_4$)alkyl.

The pH-value of the oxidizing agent containing composition is usually about 2 to 7, and in particular about 2 to 5.

One preferred method of applying formulations-comprising the dyes of formula (1a) and (1b) on the keratin-containing fiber, preferably the hair is by using a multi-compartment dyeing device or "kit" or any other multi-compartment packaging system, as described for example in WO 97/20545 on p. 4, l. 19 to l. 27.

Generally the hair is rinsed after treatment with the dyeing solution and/or permanent-wave solution.

A further preferred embodiment of the present invention relates to a method of dyeing hair with oxidative dyes, which comprises
a. mixing at least one dye of formula (1a) and (1b) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, l. 46 to l. 53 are suitable.

Furthermore, the present invention relates to a process of dyeing of keratin-containing fibers of the dyes of formula (1a) and (1b) with autooxidable compounds and optionally further dyes.

The process comprises
a. mixing at least one autooxidable compound and at least one developer compound and at least one dye of formula (1a) and (1b) and optionally further dyes, and b. treating the keratin-containing fiber with the mixture prepared in step a.

Furthermore, the present invention relates to a process for dyeing keratin-containing fibers with the dyes of formula (1a) and (1b) and capped diazotized compounds, which comprises,
a. treating the keratin-containing fibers under alkaline conditions with at least one capped diazotized compound and a coupler compound, and optionally a developer compound ad optionally an oxidizing agent, and optionally in the presence of a further dye, and optionally with at least one dye of formula (1a) and (1b), and
b. adjusting the pH in the range of 6 to 2 by treatment with an acid, optionally in the presence of a further dye, and optionally at least one dye of formula (1a) and (1b),
with the proviso that at least in one step a. or b. at least one dye of formula (1a) and (1b) is present.

The capped diazotized compound and coupler compound and optionally the oxidizing agent and developer compound can be applied in any desired order successively or simultaneously.

Preferably, the capped diazotized compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotized compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1a) and (1b) and at least one acid dye.

The following examples serve to illustrate the processes for dyeing without limiting the processes thereto. Unless specified otherwise, parts and percentages relate to weight. The amounts of dye specified are relative to the material being dyed.

EXAMPLES

A. Preparation Examples

The examples A1-A11 and A41 describe dye building blocks used for the preparation of the polymeric dyes described in this invention.

Example A1

6.6 ml 1,3-dibromopropane and 15 ml chlorobenzene are heated to 95° C. and 1.5 g of the thiazolium azo compound described in WO 2006/136617 (ex. AZO-118a) are added within 5.5 h.

After the addition, the mixture is stirred another 2 d at 95° C.

The suspension is allowed to cool to RT and filtered.

The solid is washed with diethyl ether and stirred in acetonitrile (40 ml) at 80° C. for 10 min.

The suspension is filtered at RT and the solid is stirred again in acetonitrile/ethanol (3:1) at RT for 0.5 h and filtered.

The acetonitrile and acetonitrile/ethanol filtrates are combined and evaporated to give the product of formula (BB-01) as a sticky solid.

Yield 1.74 g;

$^1$H NMR (MeOD): δ 8.24 (d, 1H), 7.95 (d, 1H), 7.80 (d, 1H), 7.56 (d, 1H), 7.19-7.12 (m, 2H), 4.75 (t, 2H), 3.56 (t, 2H), 3.45 (s, 6H), 2.53 (m, 2H); LC-MS: m/z 354 (M+).

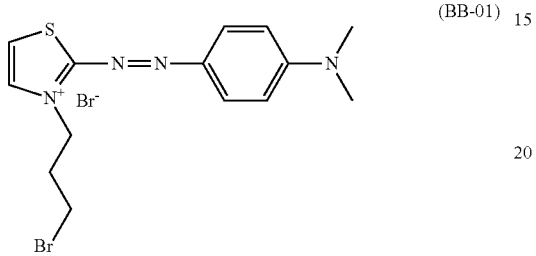

(BB-01)

Example A2

A mixture of 19.5 ml 1,3-dibromopropane, 5 g of the thiazol azo compound described in the literature (Miranda, P. C et al., Advances in Colour Science and Technology (2001), 4(1), 21-27) and 50 ml chloroform are heated to reflux for 22 h (reaction control by TLC). At RT 100 ml acetonitrile are added and an oil precipitated.

The oil is washed with acetonitrile and heated to reflux in 30 ml toluene and 4 ml acetonitrile.

The suspension is cooled to RT and filtered to obtain the product of formula (BB-02) as a dark solid.

Yield 0.82 g;

$^1$H NMR (MeOD): δ 8.25 (d, 1H), 7.93 (d, 1H), 7.79 (d, 1H), 7.54 (d, 1H), 7.19-7.12 (m, 2H), 4.74 (t, 2H), 3.81 (q, 4H), 3.56 (t, 2H), 2.52 (t, 2H), 1.37 (t, 6H); LC-MS: m/z 382 (M+).

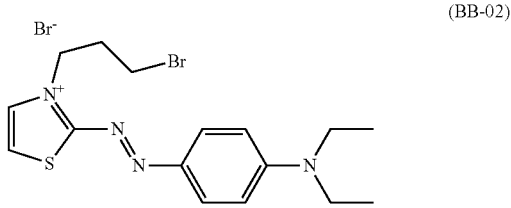

(BB-02)

Example A3

3.87 ml 1,3-dibromopropane in 10 ml methylethyl ketone are heated to 80° C.

At that temperature 1 g of the thiazol azo compound described in the literature (Mustroph H, et al., Zeitschrift für Chemie (1983), 23(8), 298-9) is added over 6 h and the mixture is stirred 16 h at 80° C. (reaction control by TLC).

The suspension is filtered at RT.

The solid is washed with methylethyl ketone and diethyl ether and dried in vacuo to obtain 1.29 g of the end product of formula (BB-03).

$^1$H NMR (MeOD): δ 8.09 (d, 1H), 7.75 (d, 1H), 7.34 (d, 1H), 6.91 (d, 1H), 6.32 (s, 1H), 4.63 (t, 2H), 4.07 (s, 3H), 3.55 (t, 2H), 3.47 (s, 6H), 2.49 (m, 2H); LC-MS: m/z 384 (M+).

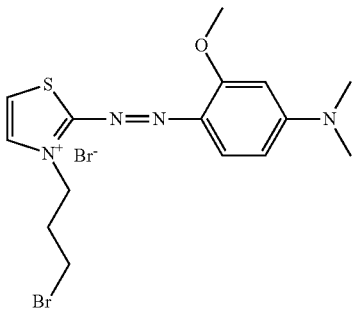

(BB-03)

Example A4

A mixture of the sulfonic acid azo dye described in WO2006/081245 (Ex. 1a), 5 ml of thienyl chloride and a few drops of DMF is stirred at room temperature for 4 h.

Then the thienyl chloride is removed under reduced pressure.

The crude product of formula (BB-04) is used without purification for the reaction with polymers containing primary and secondary nitrogen atoms.

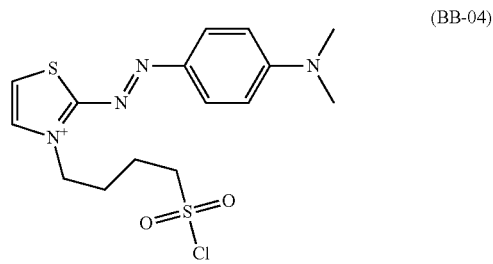

(BB-04)

Example A5

0.11 g of the thiazolium azo compound described in WO 2006/136617 (ex. AZO-120a) and 0.289 g dibromopropane are stirred in 5 ml NMP at 80° C. for 1d.

The product is collected by filtration, washed with diethyl ether and dried to obtain 0.11 g of a dark powder of formula (BB-05).

LC-MS: m/z 414, 416 (M+), UV/VIS: $\lambda_{max}$ 598 nm.

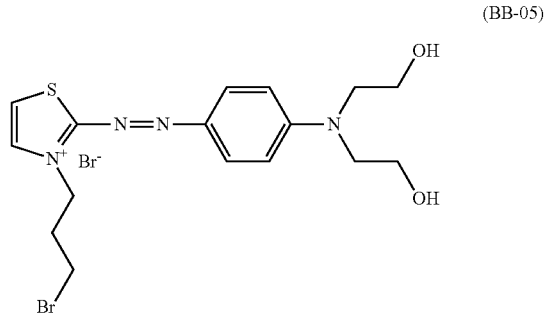

(BB-05)

Example A6

A mixture of 5 g of the thiazolium azo compound described in WO 2006/136617 (ex. AZO-118a), 3.37 ml epichlorohydrin and 18 ml acetic acid are stirred for 3.5 h at 50° C.

The solvent is evaporated under reduced pressure and the residue is treated with diethyl ether.

The obtained solid is dissolved in acetone and precipitated with diethyl ether to obtain 6.0 g of blue solid of formula (BB-06).

LC-MS: m/z 325, 327 (M+); $^1$H NMR (methanol-$d_4$): δ [ppm] 8.196 (br, 1H), 7.904 (br, 1H), 7.798 (br, 1H), 7.519 (br, 1H), 7.141 (br, 2H), 4.902 (m, 1H), 4.582 (m, 1H), 4.295 (m, 1H), 3.702 (m, 1H), 3.453 (m, 6H), 1.930 (m, 3H).

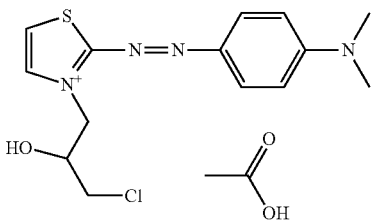

(BB-06)

Example A7

A mixture of 5.04 g of the thiazolium azo compound described in WO 2006/136617 (ex. AZO-120a) and 2.7 ml epichlorohydrin is stirred in 25 ml acetic acid for 1 h at 50° C.

The solvent is evaporated under reduced pressure and the residue is stirred in 200 ml acetone for two days.

Then the solid is collected by filtration washed with acetone and dried under reduced pressure to obtain 5.9 g of a dark solid of formula (BB-07).

$^{13}$C NMR (methanol-$d_4$): δ [ppm] 180.128, 178.585, 161.190, 147.317, 142.647, 136.319, 136.212, 124.176, 118.659, 116.865, 116.589, 71.239, 60.917, 56.367, 54.853, 47.264, 24.318. LC-MS: m/z 385, 387 (M+).

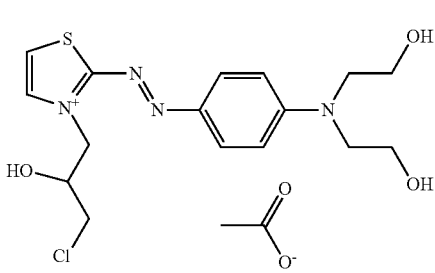

(BB-07)

Example A8

Step 1: A mixture of 30.0 g 1,4-bistosylanthrachinon (Showalter et al. Tetrahedron Letters, 26(2), 157-160, 1985) and 11.19 g 3-dimethylamino-1-propylamin in 80 ml chlorobenzene (abs.) is stirred at 100° C. for 2 h (reaction control by TLC).

The solvent is removed under reduced pressure and the crude product is purified by silica gel column chromatography (CH$_2$Cl:MeOH 15:1) to give the product as a dark red oil.
Yield: 17.17 g.

$^1$H NMR (CD$_2$Cl$_2$): δ 9.88 (s, 1H), 8.07-8.05 (d, 1H), 7.82-7.80 (d, 1H), 7.62-7.55 (m, 4H), 7.18-7.13 (m, 3H), 6.99-6.96 (d, 1H) 3.32-3.27 (m, 2H), 2.32-2.88 (t, 2H), 2.21 (s, 3H), 2.13 (s, 6H), 1.81-1.74 (m, 2H). LC-MS: m/z 479 (M+1).

Step 2: A mixture of 16.85 g of the product from step 1, 3.73 g Na$_2$CO$_3$ and 7.97 g dimethylsulfate in 750 ml methanol is stirred at RT for 18 h and at 50° C. for 2.5 h.

The solvent is removed under reduced pressure at 40° C.

The residue is washed with dichloromethane (600 ml) and then with water.

The product is dried to obtain 12.15 g of a red solid of formula (BB-10).

$^1$H NMR (CD$_3$CN): δ 9.91 (t, 1H), 8.14-8.12 (d, 1H), 7.84-7.74 (m, 3H), 7.66-7.64 (d, 2H), 7.39-7.36 (d, 1H), 7.29-7.26 (2H), 7.23-7.20 (1H) 3.54 (s, 3H), 3.51-3.39 (m, 4H), 3.09 (s, 9H), 2.27 (s, 3H). LC-MS: m/z 493 (M+).

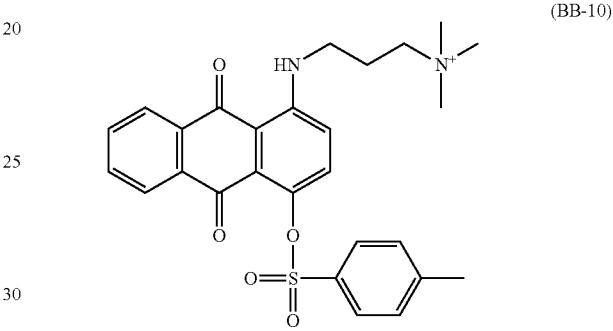

(BB-10)

Example A9

Step 1: A mixture of 30.0 g 1,4-bistosylanthrachinone (Showalter et al., Tetrahedron Lett. Vol. 26, No. 2, 157-160, 1985), 20.54 g 1-(3-aminopropyl)-imidazole and 5.53 g triethylamine in 100 ml chlorobenzene abs. is stirred at 100° C. for 1.5 h (reaction control by TLC).

The mixture is cooled to RT and poured into 160 ml hexane.

Oil and solid precipitated and the hexane is decanted.

Ethanol is added to the residue and the suspension is filtered.

The obtained solid is washed with a mixture of hexane/acetone (50:1) and once again with pure hexane.

After filtration the product is dried (red solid).
Yield: 13.0 g (47%)

$^1$H NMR (CD$_2$Cl$_2$): δ 9.89 (s, 1H), 8.07 (d, 1H, J=7.5 Hz), 7.85-7.83 (d, 1H, J=7.4), 7.64-7.62 (m, 4H), 7.39 (s, 1H), 7.20-7.15 (m, 3H), 6.94-6.82 (m, 3H), 4.06 (t, 3H, J=6.8 Hz), 3.23-3.21 (m, 2H), 2.23 (s, 1H), 2.13 (t, 2H, J=6.8 Hz). LC-MS: m/z 501 (M$^+$)

Step 2: A mixture of 1.6 g of the product obtained in step 1, 2.68 g NaHCO$_3$ and 1.0 g dimethylsulfate in 105 ml methanol/dichloromethane (2:1) are stirred at RT for 18 h and at 50° C. for 1 h.

The mixture is filtered and the solvent of the filtrate is removed under reduced pressure at 40° C.

Dichloromethane (500 ml) is added to the residue and stirred.

After filtration the solid is washed again with dichloromethane.

The washing solutions are combined and evaporated to obtain the product of formula (BB-11) as a red solid.
Yield: 1.99 g (99%), ¹H NMR (CD₂Cl₂): δ 9.78 (t, 1H, J=5.3 Hz), 9.59 (s, 1H), 8.03 (m, 1H), 7.84 (m, 1H), 7.66-7.60 (m, 4H), 7.25 (s, 1H), 7.17 (d, 2H), 7.14 (t, 1H), 7.02 (d, 1H), 4.40 (t, 2H, J=7.2), 3.89 (s, 3H), 3.56 (s, 3H), 3.44-3.39 (m, 2H), 2.31 (t, 2H, J=7.1), 2.23 (s, 3H).

Mp.: 144°-147° C. LC-MS: m/z 516 (M⁺).

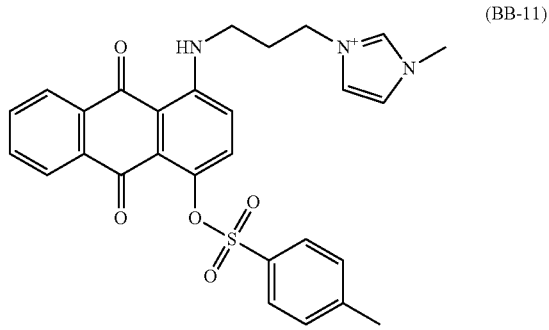

(BB-11)

Example A10

Step 1: 12.5 g of bis 2-chloroethylamine hydrochloride are solubilised in 16.5 ml of water, neutralised with 17.5 ml of NaOH 4 N aq. and the free amine is extracted 3× in 35 ml dichloromethane.

The collected solutions of amine are added dropwise to a mixture of 4.37 g (10 mmol) of 1-amino-4-bromoanthraquinone-2-sulfonyl chloride hydrochloride (CAS 40495-69-0) in 50 ml dichloromethane and 10 ml dioxane within 30 min.

The reaction mixture is heated at 39° C. for 25 h.

After cooling, 20 ml water are added and the product is filtered, taken in 8 ml of methanol and filtered again, washed with methanol.

The orange powder is dried to give 2.6 g of the 1-amino-4-bromoanthraquinone-2-sulfonic acid bis-(2-chloro-ethyl)-amide.

¹H NMR (CD₂Cl₂): ppm 3.6, m, 8H, 7.75, m, 2H, 8.1, m, 1H, 8.15, m, 1H, 8.2, s, 1H.

Step 2: 1.63 g of 1-amino-4-bromoanthraquinone-2-sulfonic acid bis-(2-chloro-ethyl)-amide are reacted with 24.2 ml pyridine at 100° C. for 3 days.

After cooling the product is filtered, washed with a mixture of 2.5 ml pyridine and 2.5 ml butanol and then twice with butanol.

After drying, 1.1 g of an orange-red powder of formula (BB-23) is obtained.

NMR: ¹H in MeOD in ppm: 4.25, t, 4H, 5.0, t, 4H, 7.85, m, 2H, 7.95-8.3, m, 7H, 8.5, m, 2H; 9.1, m, 4H.

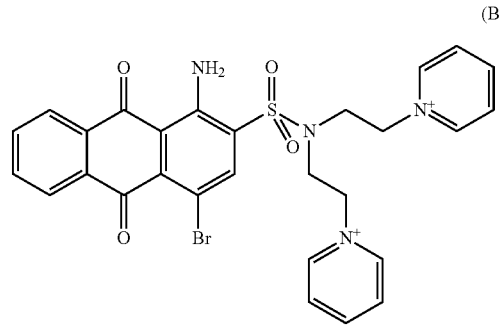

(BB-23)

Example A11

291 mg (0.696 mmol) piperazinylphenoxazine prepared as described in patent WO07039529 are solubilised in 3 ml NMP.

The solution is cooled in a bath of ice and acetone and 110 mg (0.696 mmol) of bromoacetylchloride are added.

The reaction mixture is then stirred over night at room temperature.

The product is precipitated with 15 ml ethyl acetate, filtered, washed with 20 ml ethyl acetate and dried to give 73% of the a dark blue powder of formula (BB-24).

MS (E+): m/z=413.

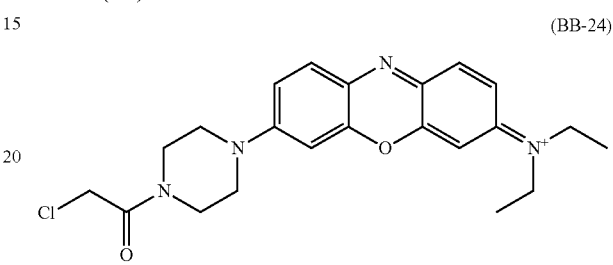

(BB-24)

The dye building blocks of formula (BB-12), (BB-13) and (BB-14) are disclosed in WO 2006/136617 and can also be used to prepare polymeric dyes:

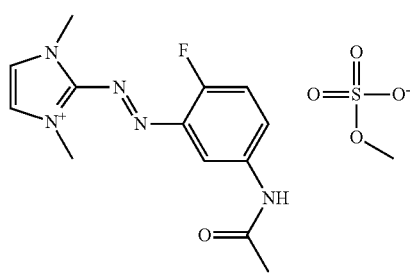

BB-12

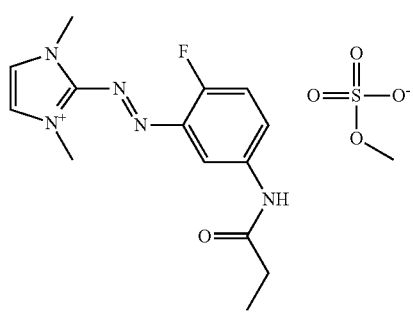

BB-13

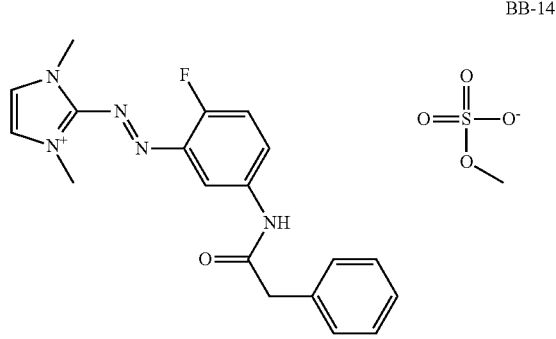

BB-14

Further polymeric dyes are also prepared by using the following dye building blocks described in EP 0 757 083:
(BB-25)
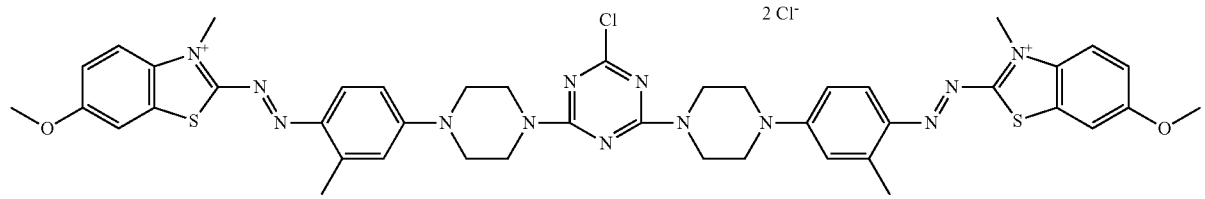
(BB-26)
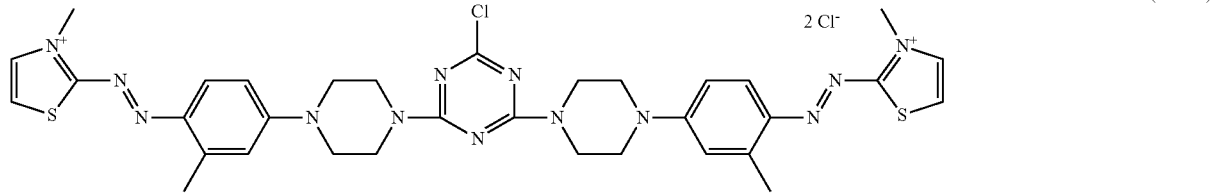
(BB-27)
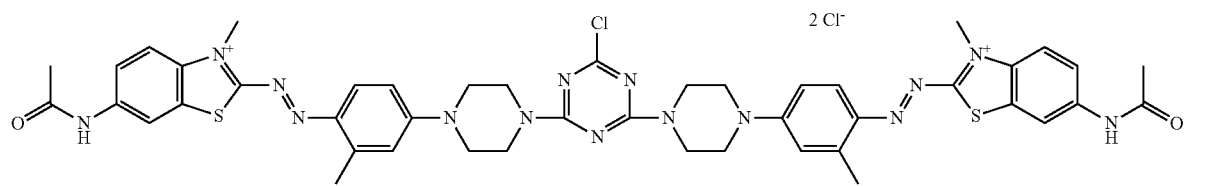
(BB-28)
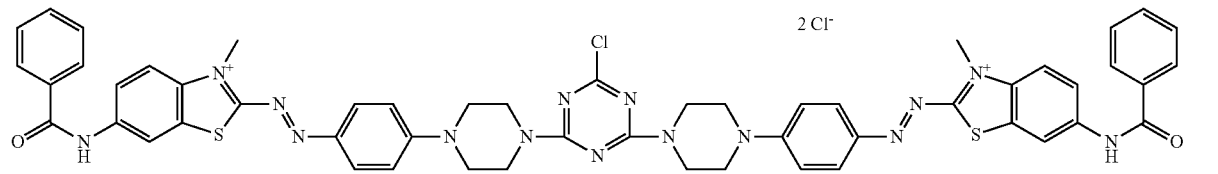
(BB-29)
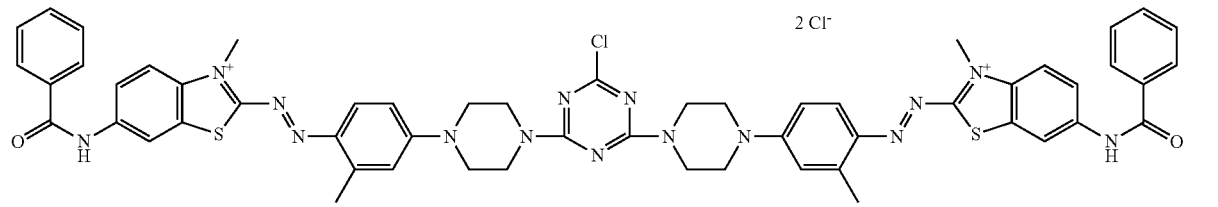
(BB-30)
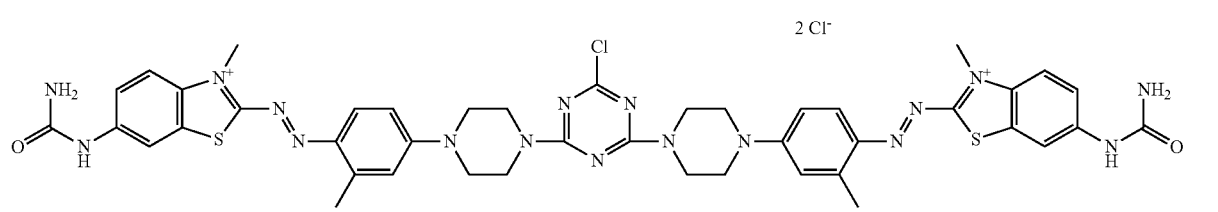
(BB-31)
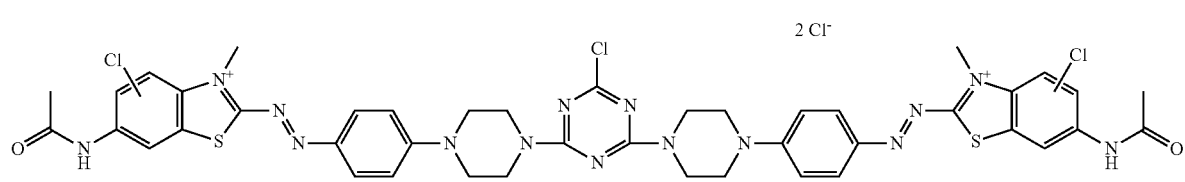

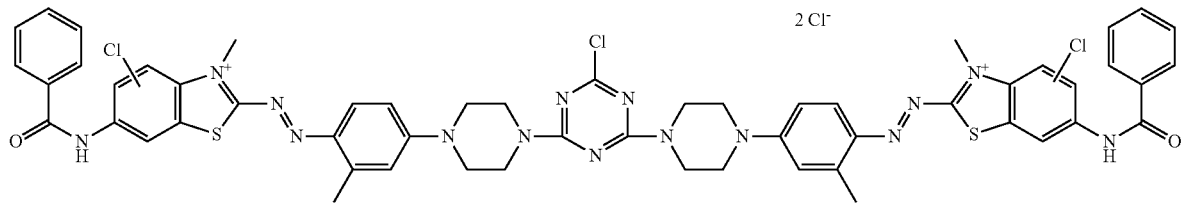

(BB-32)

The polymeric dyes described in this invention have been prepared using the following polymers:

| | |
|---|---|
| Polymer 1 | Polyethyleneimine (PEI) (Aldrich, average $M_n$ 423) |
| Polymer 2 | Polyethyleneimine (PEI) (Aldrich, average $M_n$ 600) |
| Polymer 3 | Poly-(4-vinyl-pyridin) prepared by the method described in EP1275689 and DE19909767; average number of repeating units is 36 |
| Polymer 4 | Poly-(4-vinyl-pyridin) prepared by the method described in EP1275689 and DE19909767; average number of repeating units is 48 |
| Polymer 5 | Poly-(4-vinyl-pyridin) prepared by the method described in EP1275689 and DE19909767; average number of repeating units is 76 |
| Polymer 6 | Poly-(4-vinyl-pyridin) (p-4-VP) (Aldrich, average $M_w$ 60000) |
| Polymer 7 | Poly-(4-vinyl-pyridin) (p-4-VP) (Aldrich, average $M_w$ 160000) |
| Polymer 8 | Poly-(2-dimethylaminoethyl)-acrylate (p-DMAEA) prepared by the method described in EP1275689 and DE19909767; average number of repeating units is 31 |
| Polymer 9 | (CRC 821)A mixture of 5.21 g of polymer 3 and 3.7 g of 2-chloro-ethylammonium chloride in 150 ml n-butanol is stirred under reflux for 24 h. The reaction mixture is filtered hot. The collected solid is suspended again in butanol, stirred at 50° C. and filtered again. The product is dried under vacuum to obtain 8.5 g of a colorless solid. $^1$H NMR (D$_2$O): δ [ppm] 8.65 (br), 8.14 (br), 7.58 (br), 7.02 (br), 4.78 (br), 3.59 (br), 1.82 (br) |
| Polymer 10 | Polyamine B (Akzo Nobel, Lot no: CH645628) |
| Polymer 11 | Lupasol FG (BASF) |

The polymeric dyes are prepared by reacting the described dye building blocks with the polymers 1-10 using the conditions given in Table 1. For polymeric dyes prepared from dye building blocks described in patent EP 0757083 the reaction conditions are given in table 2. The polymeric dyes have been isolated using the following workup procedures:

Workup Procedure 1:

The product is isolated by addition of diethylether.

Workup Procedure 2:

Isolation of an oil by addition of diethylether. The oil is dissolved in H$_2$O and extracted with Dichloromethane.

The product is precipitated by addition of acetonitrile to the water phase.

Workup Procedure 3:

The solvent is removed under reduced pressure. The residue is dissolved in H$_2$O and the product is precipitated by addition of acetonitrile.

Workup Procedure 4:

The solvent is removed under reduced pressure. Acetonitrile is added to the residue and the product precipitated.

Workup Procedure 5:

The product is obtained by evaporation of the solvent.

Workup Procedure 6:

The reaction mixture is cooled to room temperature and 1 eq. of hydrochloric acid (relative to the number of PEI nitrogen atoms) is added.

The precipitated product is filtered off and dried in vacuum.

Workup Procedure 7:

The product is collected by filtration, washed with acetone and dried.

TABLE 1a

Reaction conditions for the preparation of polymeric dyes

| Example | Polymer No. | Amount of Polymer | Dye No. | Amount of Dye | Solvent | T [° C.] | Time | Workup Procedure | Yield |
|---|---|---|---|---|---|---|---|---|---|
| A12 | 3 | 0.26 g | (BB-01) | 0.1 g | Isopropanol 5 ml | 40°-80° C. | 20 h | 5 | 105% |
| A13 | 3 | 0.77 g | BB-01) | 0.5 g | Isopropanol 10 ml | 80° C. | 22 h | 5 | 100% |
| A14 | 6 | 0.210 g | BB-01) | 0.434 g | Isopropanol 9 ml | 80° C. | 16 h | 1 | 73% |
| A15 | 7 | 0.210 g | BB-01) | 0.434 g | Isopropanol 9 ml | 80° C. | 16 h | 1 + purification with Isopropanol | 80% |

TABLE 1a-continued

Reaction conditions for the preparation of polymeric dyes

| Example | Polymer No. | Amount of Polymer | Dye No. | Amount of Dye | Solvent | T [° C.] | Time | Workup Procedure | Yield |
|---|---|---|---|---|---|---|---|---|---|
| A16 | 8 | 0.35 g | BB-01) | 0.1 g | Isopropanol 5 ml | 40°-80° C. | 20 h | 5 | 86% |
| A17 | 2 | 0.160 g | (BB-10) | 0.223 g | Pyridine 5 ml | 100° C. | 18 h | 1 | 78% |
| A18 | 2 | 0.199 g | (BB-10) | 0.559 g | Pyridine 5 ml | 100° C. | 18 h | 1 + isolation as hydrochloride | 22% |
| A19 | 2 | 0.33 g | (BB-11) | 0.3 g | NMP 3 ml | 80° C. | 19 h | 1 | 60% |
| A20 | 2 | 0.342 g | (BB-11) | 0.550 g | Pyridine 6 ml | 100° C. | 17 h | 5 + washed with Diethylether | 44% |
| A21 | 9 | 0.230 g | (BB-11) | 0.313 g | Methanol 10 ml | 70° C. | 18 h | 3 | 16% |
| A22 | 5 | 0.71 g | (BB-01) | 0.5 g | Isopropanol 8 ml | 80° C. | 2 d | 5 | 95% |
| A23 | 4 | 0.51 g | (BB-01) | 0.3 g | Isopropanol 10 ml | 80° C. | 1 d | 5 | 112% |
| A24 | 3 | 0.227 g | (BB-02) | 0.462 g | Isopropanol 30 ml | 80° C. | 1.5 d | 4 | 67% |
| A25 | 3 | 0.245 g | (BB-03) | 0.500 g | Isopropanol 30 ml | 80° C. | 3.5 d | 1 | 80% |
| A26 | 1 | 0.062 g | (BB-04) | 0.253 g | 1 ml CHCl$_3$, 5 ml NMP | r.t. | 1 h | 7 | 22% |
| A27 | 2 | 0.25 g | (BB-12) | 0.43 g | Isopropanol 8 ml | 40° C. | 24 h | 6 | 40% |
| A28 | 2 | 0.22 g | BB-13 | 0.43 g | Isopropanol 8 ml | 40° C. | 24 h | 6 | 66% |
| A29 | 10 | 0.22 g | BB-13 | 0.43 g | Isopropanol 6 ml | 40° C. | 6 h | 6 | 55% |
| A30 | 10 | 0.23 g | BB-14 | 0.41 g | Isopropanol | 40° C. | 12 h | 6 | 63% |

TABLE 1b

Reaction conditions for the preparation of polymeric dyes from dye building blocks described in patent EP 0757083.

| Ex. | Polymer No. | Amount of Polymer | Dye No. | Amount of Dye | Solvent | T [° C.] | Time | Workup Procedure | Yield | Product Color |
|---|---|---|---|---|---|---|---|---|---|---|
| A31 | 1 | 0.30 g | (BB-25) | 1.0 g | deionized water 15 ml | 90° C. | 5 h | 4 | 1.1 g | blue |
| A32 | 10 | 0.29 g | (BB-26) | 0.9 g | deionized water 15 ml | 90° C. | 5 h | 4 | 1.0 g | reddish blue |
| A33 | 2 | 0.32 g | (BB-27) | 1.5 g | deionized water 15 ml | 70° C. | 5 h | 5 | 1.8 g | blue |
| A34 | 2 | 0.30 g | (BB-28) | 1.3 g | deionized water 30 ml | 80° C. | 5 h | 5 | 1.6 g | blue |
| A35 | 10 | 0.28 g | (BB-29) | 1.0 g | deionized water 10 ml | 90° C. | 5 h | 5 | 1.2 g | blue |
| A36 | 2 | 0.31 g | (BB-30) | 1.1 g | deionized water 15 ml | 90° C. | 4 h | 5 | 1.4 g | blue |
| A37 | 2 | 0.30 g | (BB-31) | 2.0 g | deionized water 5 ml | 90° C. | 10 h | 5 | 2.3 g | blue |
| A38 | 10 | 0.32 g | (BB-32) | 1.8 g | deionized water 50 ml | 90° C. | 8 h | 5 | 2.1 g | blue |

TABLE 2

Analytical data

| Example | $\lambda_{max}$ (nm) | 1H NMR, δ (ppm) |
|---|---|---|
| A12 | 594 | 8.86 (br), 8.24 (br), 7.75 (br), 7.58 (br), 7.16 (br), 6.79 (br), 3.46 (br), 2.70 (br), 1.77 (br) (methanol-$d_4$) |
| A13 | 542 | 8.86 (br), 8.24 (br), 7.75 (br), 7.58 (br), 7.16 (br), 6.79 (br), 3.46 (br), 2.70 (br), 1.77 (br) (methanol-$d_4$) |
| A14 | 594 | 8.90 (vbr), 8.13(vbr), 7.57(vbr), 6.94(vbr), 2.57(vbr), 1.65(vbr) (methanol-$d_4$) |
| A15 | 595 | 8.832 (br), 8.151 (br), 7.615 (br), 7.480 (br), 7.009 (br), 6.600 (br), 4.722 (br), 3.339 (br), 2.563 (br), 1.593 (br) (methanol-$d_4$) |
| A16 | — | — |
| A17 | 589 | — |
| A18 | — | 8.609-6.271 (vbr), 4.076-2.383 (vbr), 2.120 (br) ($D_2O$) |
| A19 | 588 | — |
| A20 | — | 8.134-6.767 (vbr), 4.142-2.393 (vbr), ($D_2O$) |
| A21 | 573 | — |
| A22 | 546 | 8.873 (br), 8.219 (br), 7.598 (br), 7.128 (br), 6.766 (br), 3.441 (br), 2.746 (br), 1.749 (br), (methanol-$d_4$) |
| A23 | 548 | 8.677 (br), 8.011 (br), 7.571 (br), 7.404 (br), 6.936 (br), 6.595 (br), 3.250 (br), 1.568 (br), (methanol-$d_4$) |
| A24 | 551 | 8.794 (br), 8.278 (br), 8.094 (br), 7.636 (br), 7.472 (br), 7.131 (br), 7.027 (br), 6.760 (br), 3.705 (br), 2.611 (br), 1.720 (br), 1.245 (br), (methanol-$d_4$) |
| A25 | 531 | 8.977 (br), 8.155 (br), 7.355 (br), 6.861 (br), 6.213 (br), 3.437 (br), 2.679 (br), 1.781 (br), (methanol-$d_4$) |
| A27 | — | — |
| A28 | — | 8.026 (br), 7.777 (br), 7.403 (br), 6.903 (br), 4.642 (br), 3.620 (br), 3.366 (br), 3.228 (br), 3.063 (br), 2.867 (br), 2.289 (br) ($D_2O$) |

Example A39

0.3 g of A14 are dissolved in 5 ml methanol and 0.048 ml dimethylsulfate are added.

After stirring at room temperature for 20 h the solvent is evaporated to give the product as a dark solid.

Yield: 0.27 g.

$^1$H NMR ($D_2O$): δ [ppm] 8.414 (br), 7.682 (br), 7.323 (br), 6.985 (br), 4.117 (br), 3.582 (br), 3.278 (br), 2.493 (br), 1.643 (br).

Example A40

0.3 g of A15 are dissolved in 5 ml methanol and 0.048 ml dimethylsulfate ware added.

After stirring at room temperature for 20 h the solvent is evaporated to give the product as a dark solid.

Yield: 0.33 g.

$^1$H NMR ($D_2O$): δ [ppm] 8.462 (br), 7.852 (br), 7.687 (br), 7.298 (br), 6.888 (br), 4.114 (br), 3.630 (br), 3.240 (br), 2.474 (br), 1.674 (br), 1.091 (br).

Example A41

A mixture of 0.5 g of the thiazolium azo base (CAS 3771-31-1) and 1.63 ml 1,3-dibromopropane in 5 ml chlorobenzene is stirred for 24 h at 100° C.

The reaction mixture is cooled to room temperature and filtered.

The filter cake is washed with chlorobenzene, toluene and diethylether and dried under reduced pressure to obtain 0.69 g of a black powder of formula (BB-08).

This reactive dye building block can also used for the preparation of polymeric dyes.

LC-MS (ES+): m/z 434, 436 (1:1).

UV/VIS: $\lambda_{max}$ 585 nm.

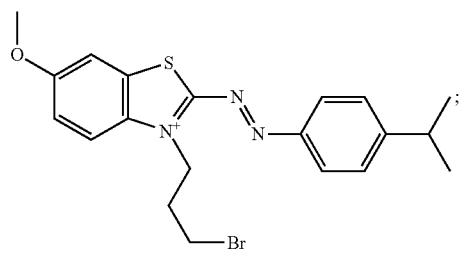

(BB-08)

Example A42

0.063 g of polymer 2 are dissolved in 1.5 ml water. 0.31 g of dye BB-23, 0.128 g of potassium carbonate, 0.007 g copper and 0.01 g copper (I) chloride are added.

The reaction mixture is stirred at 80° C. for 4 h.

After cooling, the reaction mixture is evaporated to dryness, the residue is taken in methanol and clarified.

The methanol solution is then evaporated and the solid is washed twice with dichloromethane and ethyl acetate and dried to give 0.25 g of a dark powder, which can be used for dyeing hair in grayish blue shades.

Example A43

Step 1

A solution of 2.37 g 1-amino-4-(3-dimethylaminopropyl) amino-anthraquinone (CAS-no. 65274-31-9) and 7.5 ml dibromopropane in 30 ml of chloroform is stirred for 16 h at 60° C.

After cooling of the reaction mixture to room temperature, the product is filtered off and dried under vacuum at 30° C. to yield 3.25 g of a blue powder of formula BB-33.

MS (ES+): m/z 444, 446. UV/VIS (methanol): λmax 603 nm. ¹H NMR (dmso-d6): δ [ppm] 10.84 (t, H), 8.45 (br, 2H) 8.24 (m, 2H) 7.82 (m, 2H), 7.50 (d, 2H), 7.37 (d, 2H), 3.59 (m, 2H), 3.52 (m, 2H), 3.43 (m, 4H), 3.10 (s, 6H), 2.30 (m, 2H), 2.10 (m, 2H).

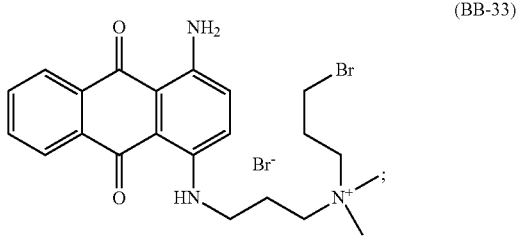
(BB-33)

Step 2

0.95 g of BB-33 from step 1 and 0.345 g of polymer 11 are mixed with 30 ml of chloroform.

The mixture is stirred for 3 days at 50° C., then it is cooled to room temperature and the precipitate is collected by filtration.

The solid is dried under reduced pressure at 40° C. to yield 1.05 g of a black solid.

¹H NMR (DMSO-d₆): δ [ppm] 10.77 (br, 1H), 8.4 (br, 2H), 8.22 (br, 2H), 7.76 (br, 2H), 7.4 (m, 2H), 3.54 (br), 3.08 (br), 2.86-2.62 (br), 2.08 (br), 1.85 (br).

Example A 44

Step 1

15.1 g of 1-amino-4-(3-dimethylaminopropyl)amino-anthraquinone (CAS-no. 65274-31-9) and 23.3 g NaHCO₃ are dissolved in 100 ml of methanol.

Then 6.9 ml of dimethyl sulfate are added slowly.

The reaction mixture is stirred for 26 h at 30 to 40° C.

Then the inorganic salts are removed by filtration and the solvent is removed under reduced pressure.

The residue is washed with tert.-butyl methyl ether and dimethyl ether and finally dried to yield 18.8 g of a dark blue solid of formula BB-34.

MS (ES+): m/z 338 (M+)
UV/VIS (methanol): λmax 610 nm.
¹H NMR (D₂O): δ [ppm] 7.43-7.19 (m, 4H), 6.10 (d, 1H), 6.05 (d, 1H), 3.72 (s, 6H), 3.51 (s, 1H), 3.32 (s, 3H), 3.18 (m, 2H) 3.10 (s, 9H), 2.53 (br, 2H), 1.68 (br, 2H).

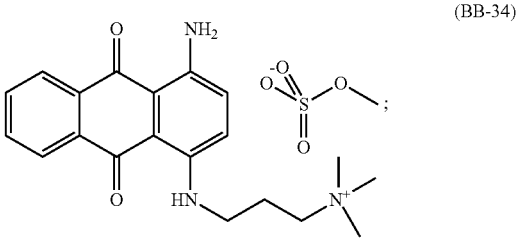
(BB-34)

Step 2

0.21 g of BB-34 from step 1 and 0.06 g cyanuric chloride are mixed in 20 ml of water.

Then the reaction mixture is stirred for 1 h at 50° C., maintaining a pH value of 7.

Then 0.112 g of polymer 2 are added and the reaction mixture is stirred 3 h at 90° C.

Then the solvent is removed under reduced pressure to obtain 0.116 g of a dark solid.

Example A45

A solution of 0.071 g of Jeffamine T-403 [39423-51-3] (0.45 mmol) and 0.236 g of BB-33 (0.45 mmol) in a mixture of 4 ml ethanol and 6 ml of acetonitrile in the presence of 0.048 g of triethylamine (0.47 mmol) were stirred at 75° for 30 h. After cooling, the reaction mixture was diluted with 12 ml of ethyl acetate and the precipitated solid was filtered off and washed with ethyl acetate. The polymer was dried under vacuum to give 0.124 g (46%) of a dark blue powder.

Example A46

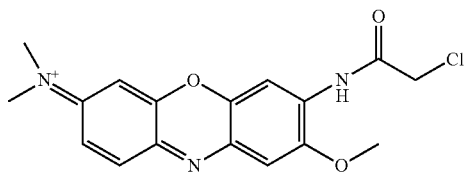
BB-34

A solution of 0.4 g of BB 124 (1.3 mmol) and 2.96 g chloroacetylchloride (26.2 mmol) in 4 ml acetonitrile was stirred at 40° C. for 4 h. After cooling, the reaction mixture was diluted with 60 ml ethyl acetate. The precipitated solid was filtered off and washed twice with ethyl acetate to give after drying under vacuum 0.34 g (68%) of a dark blue powder of formula BB-34.

MS (ES+): m/z 346. UV/VIS (methanol): λmax 581 nm.
1H NMR (MeOD): δ [ppm] 8.8 (s, 1H), 7.9 (m, 2H), 7.65 (s, 1H), 7.2 (s, 1H), 4.5 (s, 2H), 4.15 (s, 3H), 3.6 (s, 6H)

Example A47

0.068 g of Polyamine B (Akzo Nobel) (1.59 mmol eq. N) were reacted with 0.2 g of the derivative of formula BB-34 (0.5 mmol) in 2 ml of methanol at 55° C. for 21 h. 4 h. After cooling, the reaction mixture was diluted with 8 ml ethyl acetate. The precipitated solid was filtered off and washed twice with ethyl acetate. The solid obtained was dried under vacuum to give 0.19 g (76%) of a dark blue powder.

¹H NMR (MeOD): δ [ppm] 8.8-6.2 (br, 5H), 4.4-2.3 (br, 50H)

Example A48

Step 1

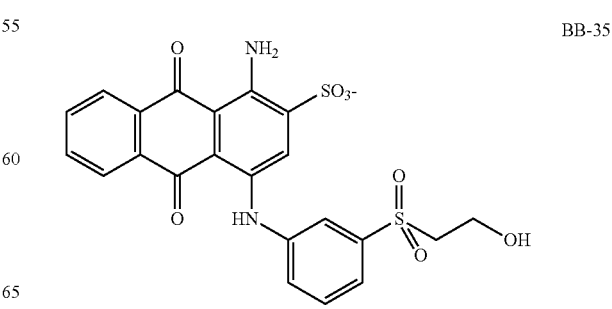
BB-35

21.14 g of bromoaminic acid (50 mmol) were stirred with 180 water at room temperature over night. 11.89 g of 2-(3-aminophenylsulphonyl)ethanol hydrochloride [19076-03-0] (50 mmol) and 1.19 g lithium hydroxide solubilized in 15 ml water (50 mmol) were added followed by 14 g of sodium hydrogen carbonate. The reaction mixture was then heated to 60° C. 12 ml of a water solution of 1 g of copper (II) sulfate.5 H2O (4 mmol) and 5 g of glucose. 1 H2O were added in 4 portions over 5 h at 60° C. After the reaction, 6.3 ml of 60% sulfuric acid were added producing a gas evolution. When it stopped, the reaction mixture was filtered at 60° C., and washed with 20 ml water, 200 ml methanol and again 500 ml water giving after drying under vacuum, 24.3 g (90%) of the coupling product of formula BB-35.

MS (ES+): m/z 503, 1H NMR (DMSO-d6): δ [ppm] 11.85 (s, 1H), 10.0 (s, 1H), 8.3 (t, 2H), 8.1 (s, 1H), 7.9 (m, 2H), 7.75 (s, 1H), 7.65 (m, 3H), 7.5 (s, 1H), 4.9 (t, 1H), 3.75 (m, 2H), 3.5 (t, 2H).

Step 2

BB-36

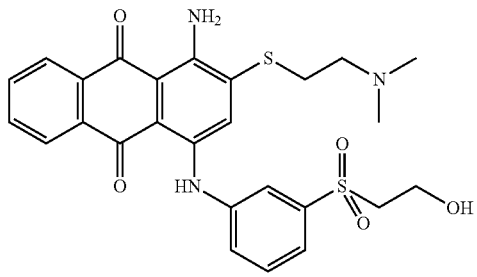

2.48 g of thiourea [62-56-6] (32.6 mmol) and 4.7 g of N-(2-Chloroethyl)-N,N-dimethylammonium chloride [4584-46-7] (32.6 mmol) were stirred in 135 g water under reflux for 16 h. A 36% sodium hydroxide solution was added until the reaction mixture reached a pH of 11. Then 10.48 g the product of formula BB-35 (20 mmol) were added and the reaction mixture was stirred under reflux for an additional 8 h. After cooling, the reaction mixture was filtered and washed with 50 ml water/methanol (1/1), and 50 ml methanol. After drying under vacuum, 8.54 g (81%) of the product of formula BB-36 were obtained.

MS (ES+): m/z 526. 1H NMR (DMSO-d6): δ [ppm] 12.2 (s, 1H), 8.5 (s, 2H), 8.25 (m, 2H), 7.85 (m, 3H), 7.55 (m, 3H), 7.4 (s, 1H) 4.9 (t, 1H), 3.75 (q, 2H), 3.55 (m, 2H), 3.2 (t, 2H), 2.6 m, 2H), 2.15 (s, 6H)

Step 3

BB-37

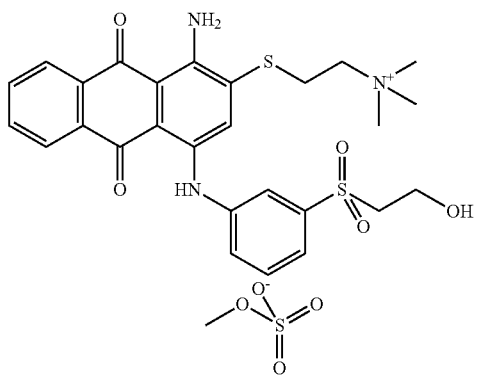

8.25 g of product of formula BB-36 (16.2 mmol) are suspended in 270 ml toluene and heated to 70° C. 1.69 ml of dimethylsulfate [77-78-1] (17.8 mmol) were added drop wise over 3 h at 70° C. and stirred for 2.5 h at 73° C. After cooling to room temperature, it was filtered off and washed with 200 ml isopropanol. After drying under vacuum, 10.11 g (95%) of a dark blue powder of formula BB-37 were obtained.

MS (ES+): m/z 540. 1H NMR (DMSO-d6): δ [ppm] 11.9 (s, 1H), 8.5 (s, 2H), 8.3 (m, 2H), 7.9 (m, 3H), 7.75 (s, 1H), 7.65 (m, 3H), 4.9 (s, 1H), 3.75 (q, 2H), 3.5 (m, 6H), 3.4 (s, 3H), 3.05 (s, 9H)

Step 4

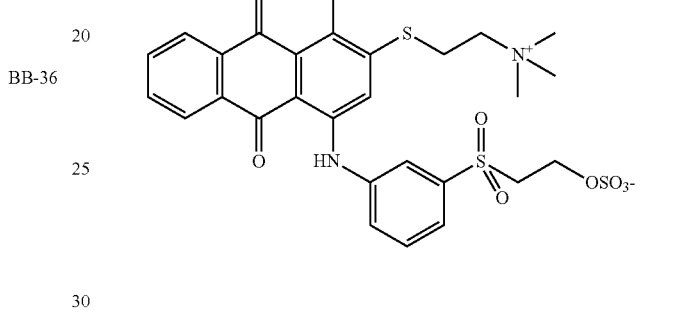

10.04 g of the product of formula BB-37 (15.4 mmol) were cooled in a ice bath. 38.7 g sulfuric acid 25% SO3 fuming [8014-95-7] were added and the reaction mixture was stirred for 24 h at room temperature. The reaction mixture was then added drop wise to a flask containing 187 g of ice and then stirred for 10 minutes. The solid obtained was filtered and washed to give 8.6 g (90%) of the product of formula BB-38.

1H NMR (DMSO-d6): δ [ppm] 11.95 (s, 1H), 8.45 (s, 1H), 8.25 (m, 2H), 7.9 (m, 3H), 7.7 (m, 4H)

Example A49

3.93 g of the product of formula BB-38 (6.35 mmol) were stirred in 60 ml methanol and 2.73 g of polyethyleneimine (Aldrich Mn=423) (63.45 mmol N) were added and the reaction mixture was stirred for 4 h at 65° C. The reaction mixture was decanted and the solution was evaporated to dryness giving 4.79 g of blue polymer.

1H NMR (D2O): δ [ppm] 8.2-6.8 (br, 9H), 4.0-2.8 (br, 89H)

Example A50

0.034 g of Jeffamine (6.31 mmol N/g pol) [39423-51-3] were reacted with 0.2 g of the product of formula BB-38 (0.323 mmol) in a mixture of 1.5 ml methanol and 1.5 ml acetonitrile in the presence of 0.023 g of triethylamine (0.226 mmol) at 60° C. for 23 h. The reaction mixture was then diluted with 20 ml methanol. The polymer was filtered off and washed with methanol. After drying under vacuum, 0.105 g (49%) of a dark blue powder was obtained.

1H NMR (DMSO-d6): δ [ppm] 8.2-6.6 (br, 9H), 4.2-2.6 (br, 29H), 1.4-0.5 (br, 13H)

Example A51

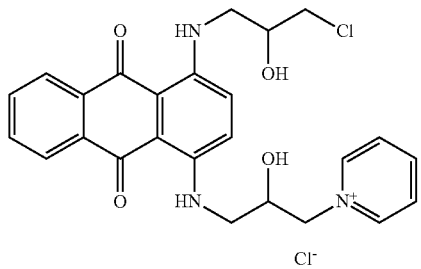

A mixture 1.27 g of 1,4-Bis[(3-chloro-2-hydroxypropyl)amino]-9,10-anthracenedione (30 mmol) prepared as described in *J. Med. Chem.* 1992, vol. 35, no 23, 4259-4263 in 12.7 ml of pyridine and 12.7 ml of toluene was heated at 100° C. under nitrogen atmosphere for 2 days. After cooling, the reaction mixture was evaporated to dryness and recrystallized with a mixture of dioxane and methanol (1/1). The solid was filtered off and washed with dioxane. After drying under vacuum, 1.08 g of a dark blue powder of formula BB-39 was obtained yielding 72%. MS (ES+): m/z 465. 1H NMR (dmso-d6): δ [ppm] 10.95 (s, 1H), 9.03 (d, 2H), 8.60 (t, 1H), 8.25 (m, 2H), 8.20 (t, 2H), 7.8 (m, 2H), 7.6 (dd, 2H), 6.05-5.75, (br, 2H), 4.9 (d, 1H), 4.5 (m, 1H), 4.2 (br 1H), 3.9 (br, 1H), 3.8-3.4 (br, 6H)

Example A52

A solution of 0.063 g of Polyamine B (Akzo Nobel) (1.47 mmol) and 0.270 g of product of formula BB-39 (0.485 mmol) were reacted in 1 ml of 1-butanol at 100° C. for 2 days. The butanol was evaporated and the reaction mixture was taken in 20 ml ethanol.

The solid was filtered off and washed with ethanol. After drying under vacuum, 0.124 g (40%) of a dark blue powder were obtained.

1H NMR (D2O): δ [ppm] 9.0-6.4 (br, 11H), 4.2-2.4 (b, 33H)

Example A53

Same procedure as A52 using Lupasol instead of Polyamine B. 0.140 g (45%) of polymer were obtained.

1H NMR (D2O): δ [ppm] 9.0-6.2 (br, 11H), 4.2-2.4 (b, 34H)

B. Application Examples

Hair Samples

For the application examples the following hair types have been used:

1 blonde hair tress (VIRGIN White Hair from IMHAIR Ltd., via G. Verga 8, 90134 Palermo (Italy)), 1 middle blonde hair tress (UNA-Europ. nature hair, Color middle blonde from Fischbach & Miller, Postfach 1163, 88461 Laupheim, Germany), 1 bleached hair tress (UNA-Europ. nature hair, Color white bleached blonde from Fischbach & Miller, Postfach 1163, 88461 Laupheim, Germany).

Coloring Solution:

0.1% w/w of one of the dyes described in examples A10 to A29 are dissolved in a Plantaren solution (10% w/w Plantacare 200UP (ID: 185971.5) in water; pH adjusted to 9.5 with 50% citric acid solution or monoethanolamine solution).

For some examples different solvents or solvent mixtures are used, which are given in Table 3.

Dyeing Procedure:

The hair tresses are dyed according to the following procedure:

The coloring solution is applied directly to the dry hair, incubated for 20 min. at room temperature, and then rinsed off under tap water (water temperature: 37° C.+/−1° C.; flow rate of water: 5-6 l/min.).

Then the tresses are pressed out with a paper towel and dried over night at room temperature on a glass plate.

Wash Fastness

For determination of the wash fastness two sets of hair tresses are dyed under the same conditions.

One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min).

Finally the tresses are rinsed under tap water, pressed out with a paper towel, combed and dried with a hair dryer or at room temperature.

This procedure is repeated 10 times.

The color position of the colored hair tresses in the CIELAB color coordinate system can be determined spectrophotometrically giving the rectangular coordinates L* (Lightness), a* and b* or alternatively the polar coordinates L*, C* (chroma) and h (hue) [W. Herbst & K. Hunger in Industrial Organic Pigments, VCH Verlagsgesellschaft, 2nd Ed. 1997, page 50 and references therein.

Another reference would be M.-Bohnert et al., Rechtsmedizin (1998) 8, 207-211].

The colorimetric reflectance measurements are conducted with the following spectrophotometer: "Datacolor Spectraflash SF 450" equipped with a xenon light source filtered to D65 with a measurement geometry of diffuse illumination and 8° viewing.

The measurements of the hair tresses are conducted directly on the measure head using the plate with an aperture (hole) of 6.6 mm.

The measurements are conducted 8 times and the average values used.

Before the measurements, the spectrophotometer was calibrated using a black and a white standard provided by Datacolor.

Then the color loss of the set of washed tresses relative to the set of unwashed tresses is evaluated using the Grey Scale according to: Industrial Organic Pigments by Herbst&Hunger, 2nd ed., p. 61, Nr 10: DIN 54 001-8-1982, "Herstellung und Bewertung der Änderung der Farbe", ISO 105-A02-1993.

TABLE 3

Results for Application Examples B1-B31

| Example | Dye | Solvent | Hair Type | Color | Intensity | Brilliance | hue[1] | Wash-fastness Grey scale |
|---|---|---|---|---|---|---|---|---|
| B1 | A12 | Coloring Solution | blond | blue | moderate | moderate | | 3 |
| | | | middle blond | blue | good | good | | 3-4 |
| | | | bleached | blue | good | good | 284 | 3 |
| B2 | A13 | EtOH/Plantaren 1:4 | blond | blue | good | good | | 3 |
| | | | middle blond | blue | moderate | moderate | | 4-5 |
| | | | bleached | blue | good | good | 299 | 3 |
| B3 | A14 | EtOH/Plantaren 1:4 | blond | blue | good | good | | 3 |
| | | | middle blond | blue | good | good | | 3-4 |
| | | | bleached | blue | good | good | 306 | 3 |
| B4 | A15 | EtOH/Plantaren 1:4 | blond | blue | good | good | | 3 |
| | | | middle blond | blue | good | good | | 3 |
| | | | bleached | blue | good | good | 305 | 3 |
| B5 | A16 | Coloring Solution | blond | violet | moderate | moderate | | 3 |
| | | | middle blond | violet | moderate | moderate | | 3-4 |
| | | | bleached | violet | moderate | moderate | 310 | 3-4 |
| B6 | A17 | Coloring Solution | blond | blue | moderate | moderate | | 3 |
| | | | middle blond | blue | moderate | moderate | | 3-4 |
| | | | bleached | blue | moderate | moderate | 287 | 4 |
| B7 | A19 | Coloring Solution | blond | blue | moderate | moderate | | 4 |
| | | | middle blond | blue | moderate | moderate | | 4 |
| | | | bleached | blue | good | good | 278 | 3-4 |
| B8 | A20 | Coloring Solution | blond | blue | moderate | moderate | | 3 |
| | | | middle blond | blue | moderate | moderate | | 3-4 |
| | | | bleached | blue | good | moderate | 276 | 3-4 |
| B9 | A20 | Coloring Solution with 0.5% dye | blond | blue | moderate | good | | 3 |
| | | | middle blond | blue | moderate | good | | 3-4 |
| | | | bleached | blue | good | good | 281 | 4-5 |
| B10 | A21 | Coloring Solution | blond | blue | bad | bad | | — |
| | | | middle blond | blue | bad | bad | | — |
| | | | bleached | blue | bad | bad | — | — |
| B11 | A23 | EtOH/Plantaren 1:4 | blond | blue | good | good | | 3 |
| | | | middle blond | blue | good | good | | 4 |
| | | | bleached | blue | good | good | 299 | 3 |
| B12 | A24 | EtOH/Plantaren 1:4 | blond | blue | good | good | | 2-3 |
| | | | middle blond | blue | good | good | | 3 |
| | | | bleached | blue | good | good | 292 | 3 |
| B13 | A25 | EtOH/Plantaren 1:4 | blond | violet | good | good | | 2-3 |
| | | | middle blond | violet | good | good | | 2-3 |
| | | | bleached | violet | good | good | 313 | 2-3 |
| B14 | A26 | Coloring Solution | blond | blue | bad | bad | | 1 |
| | | | middle blond | blue | moderate | moderate | | 1 |
| | | | bleached | blue | bad | bad | — | 1 |
| B15 | A27 | Coloring Solution | blond | blue | moderate | moderate | | 4-5 |
| | | | middle blond | blue | moderate | moderate | | 4-5 |
| | | | bleached | blue | moderate | moderate | 261 | 3 |
| B16 | A28 | Coloring Solution | blond | blue | moderate | moderate | | 4-5 |
| | | | middle blond | blue | moderate | moderate | | 4 |
| | | | bleached | blue | moderate | moderate | 268 | 3-4 |
| B17 | A29 | Coloring Solution | blond | blue | moderate | moderate | | 3 |
| | | | middle blond | blue | moderate | moderate | | 3 |
| | | | bleached | blue | good | good | 281 | 3 |
| B18 | A30 | Deionized water | blond | blue | good | moderate | | 3 |
| | | | middle blond | blue | good | moderate | | 3-4 |
| | | | bleached | blue | good | moderate | 289 | 3-4 |

TABLE 3-continued

Results for Application Examples B1-B31

| Example | Dye | Solvent | Hair Type | Color | Intensity | Brilliance | hue[1] | Wash-fastness Grey scale |
|---|---|---|---|---|---|---|---|---|
| B19 | A31 | Deionized water | blond | violet | good | good | | 4 |
| | | | middle blond | violet | good | good | | 2-3 |
| | | | bleached blond | violet | good | good | 305 | 2-3 |
| B33 | A43 | | blond | blue | good | good | | 3 |
| | | | middle blond | blue | good | good | | 4 |
| | | | bleached blond | blue | good | good | 270 | 3 |
| B34 | A44 | | blond | blue | moderate | moderate | | 2 |
| | | | middle blond | blue | moderate | moderate | | 4 |
| | | | bleached blond | blue | moderate | moderate | 270 | 2 |
| B35 | A45 | | blond | blue | moderate | moderate | | 3-4 |
| | | | middle blond | blue | moderate | good | | 3 |
| | | | bleached blond | blue | good | good | 286 | 3 |
| B36 | A47 | | blond | blue | good | good | | 4 |
| | | | middle blond | blue | good | good | | 4 |
| | | | bleached blond | blue | good | good | 250 | 4 |
| B37 | A49 | | blond | blue | moderate | good | | 3-4 |
| | | | middle blond | blue | moderate | good | | 4-5 |
| | | | bleached blond | blue | moderate | good | 259 | 3 |
| B38 | A50 | | blond | blue | moderate | moderate | | 3 |
| | | | middle blond | blue | moderate | good | | 4 |
| | | | bleached blond | blue | good | good | 261 | 3-4 |
| B39 | A52 | | blond | blue | good | good | | 3-4 |
| | | | middle blond | blue | good | good | | 3-4 |
| | | | bleached blond | blue | good | good | 263 | 3-4 |
| B40 | A53 | | blond | blue | moderate | good | | 3-4 |
| | | | middle blond3 | blue | moderate | moderate | | 3-4 |
| | | | bleached blond | blue | good | good | 263 | |

[1] on bleached tresses.

Mixtures of Polymeric Dyes:

A dye emulsion, pH=10.5

| INGREDIENT | w/w % |
|---|---|
| Mixture of dyes as described in table 4 and 5 | x |
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Deionized Water 70° C. | ad 100.00 | is mixed with 1.5 wt. % of a 9% hydrogen peroxide solution and the mixture is immediately applied to a tress of brown hair.

After 30 minutes the tress is rinsed, shampooed, rinsed and dried.

The color of the dyed tresses is given in Tables 4 and 5.

TABLE 4

Mixtures of polymeric dyes.

| Comp. of formula | Color | Formulation No.: B20 | B21 | B22 | B23 | B24 |
|---|---|---|---|---|---|---|
| A28-EP2007/056945 [2] | yellow | 0.1 | 5.0 | | | 0.03 |
| A23-EP2007/056945 [2] | orange | 1.0 | | 0.4 | 0.07 | |
| A7-EP2007/056945 [2] | red | | 0.5 | | | 0.03 |
| A9-EP2007/056945 [2] | red | | | 0.3 | | |
| A15-EP2007/056945 [2] | red | | | | 0.01 | |
| A15 | blue | 1.0 | | | | 0.03 |
| A20 | blue | | 2.0 | | | |
| A23 | blue | | | 0.1 | | |
| A40 | blue | | | | | 0.03 |
| Total dye content X | | 0.3 | 7.5 | 0.8 | 0.11 | 0.09 |
| Color result on bleached hair [1] | | S | B | B | B | B |

[1] S = black, B = brown

[2] Polymeric dyes described in patent application no. EP2007/056945.

TABLE 5

Mixtures of polymeric dyes and direct dyes.

| Comp. of formula | Color | B25 | B26 | B27 | B28 | B29 | B30 | B31 | B32 |
|---|---|---|---|---|---|---|---|---|---|
| A15 | blue |  | 2.0 |  | 0.2 | 0.01 | 1.6 | 0.1 | 0.2 |
| A20 | blue | 0.1 |  | 0.5 |  | 1.0 |  |  |  |
| Direct Dye |  |  |  |  |  |  |  |  |  |
| Basic Yellow 57 |  |  | 5.0 |  |  | 0.4 | 2.0 | 0.5 |  |
| Basic Red 76 |  | 0.2 |  |  | 0.2 |  | 0.3 |  |  |
| HC Red No. 3 |  |  |  |  | 0.1 |  | 0.1 |  |  |
| HC Red BN |  |  | 0.5 |  |  |  | 0.1 |  | 0.1 |
| Basic Brown 16 |  | 0.1 |  |  |  | 0.5 |  |  |  |
| Basic Brown 17 |  | 0.1 |  |  |  | 0.5 | 2.0 |  | 0.5 |
| Total dye content X |  | 0.5 | 7.5 | 0.6 | 0.4 | 2.41 | 0.5 | 0.3 | 0.8 |
| Color result on bleached hair [1)] |  | B | B | V | V | B | S | G | B |

[1)] S = black, B = brown, V = violet, G = green

Example B 33

A dying is prepared by mixing
1 part of a red solution (0.1 w. % coloring solution of example A7 from patent application EP2007/056945),
4 parts of a yellow solution (0.1 w. % coloring solution of example A28 from patent application EP2007/056945) and
4 parts of a blue solution (0.1 w. % coloring solution of example A15).

This solution is applied to blond, middle blond and bleached hair as described above.

All three strands are dyed in a dark brown shade.

Example B34

A dying is prepared by mixing
1 part of a red solution (0.1 w. % coloring solution of example A7 from patent application EP2007/056945),
4 parts of a yellow solution (0.1 w. % coloring solution of example A28 from patent application EP2007/056945) and
4 parts of a blue solution (0.3 w. % coloring solution of example A20).

This solution is applied to blond, middle blond and bleached hair as described above. All three strands are dyed in a brown shade.

The invention claimed is:

1. Cationic polymeric dye with a hue value of h=210° to 330°, comprising
   (a) a polymer backbone,
   (b) a residue of an organic dye, and
   (c) optionally colorless organic groups,
   wherein (b) and (c) are covalently bound to the polymer backbone (a), the cationic charges can independently be part of the dye or the colorless organic groups and the residues of the organic dyes (b) are selected from the group consisting of 1,4-diamino-anthraquinone, thiazolazo, benzothiazolazo, thiadiazolazo and imidazolazo dyes.

2. Polymeric dye according to claim 1, wherein 1 to 3 different residues of an organic dye (b) are bound to the polymer backbone (a).

3. Polymeric dye according to claim 1, wherein the polymer backbone (a) is selected from polyethyleneimine, polypropyleneimine, polyvinylamine; polyvinylimine; polysiloxane; polystyrene, polyvinylimidazol, polyvinylpyridine, poly-DADMAC, polyvinylalcohol, polyacrylate, polymethacrylate; polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polysaccharide, starch, cellulose, lignin; and copolymers and blends of the mentioned polymers.

4. Polymeric dye according to claim 1 which corresponds to the formula

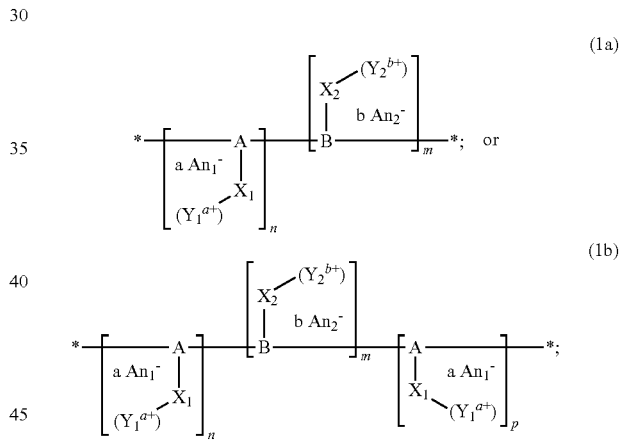

wherein
A and B, independently from each other represent a polymer backbone (a);
$X_1$ and $X_2$, independently from each other are a linkage group selected from —$C_1$-$C_{30}$alkylene-, —$C_2$-$C_{12}$alkenylene-, —$C_5$-$C_{10}$arylene, —$C_5$-$C_{10}$cycloalkylene or —$C_1$-$C_{10}$alkylene($C_5$-$C_{10}$arylene) which may be interrupted and/or terminated at one or both ends by one or more than one —O—, —S—, —N=, —N($R_1$)—, S(O)—, —SO$_2$—, —(CH$_2$CH$_2$—O)$_{1\text{-}5}$—, —(CH$_2$CH$_2$CH$_2$—O)$_{1\text{-}5}$—, —C(O)—, —C(O)O—, —OC(O)—,

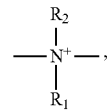

—CON(R$_1$)—, —C(NR$_1$R$_2$)$_2$—, —(R$_1$)NC(O)—, —C(S)R$_1$— or an optionally substituted, saturated or unsaturated, fused or non-fused aromatic or nonaromatic (hetero)cyclic bivalent radical optionally comprising at least one heteroatom; —O—; —S—; —N(R$_1$)—; —S(O)—; SO$_2$—; —(CH$_2$CH$_2$—O)$_{1-5}$—; —C(O)—; —C(O)O—, —OC(O)—;

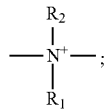

—C(O)N(R$_1$)—; S(O)$_2$N(R$_1$)—; —C(NR$_1$R$_2$)$_2$—; —(R$_1$)NC(O)—; —C(S)R$_1$—;

saturated or unsaturated, fused or non-fused aromatic or nonaromatic bivalent radical optionally comprising at least one heteroatom, which is optionally substituted by C$_1$-C$_{30}$alkyl, C$_1$-C$_{30}$alkoxy, C$_2$-C$_{12}$alkenyl, C$_5$-C$_{10}$aryl, C$_5$-C$_{10}$cycloalkyl, C$_1$-C$_{10}$alkyl(C$_5$-C$_{10}$arylene), halogen, hydroxy; or the direct bond;

R$_1$ and R$_2$ independently from each other hydrogen; unsubstituted or substituted, straight-chain or branched, monocyclic or polycyclic, interrupted or uninterrupted C$_1$-C$_{14}$alkyl; C$_1$-C$_{14}$ hydroxyalkyl; C$_1$-C$_{14}$-aminoalkyl; C$_2$-C$_{14}$alkenyl; C$_6$-C$_{10}$aryl; C$_6$-C$_{10}$aryl-C$_1$-C$_{10}$alkyl; or C$_5$-C$_{10}$alkyl(C$_5$-C$_{10}$aryl);

Y$_1$ and Y$_2$ independently from each other are a residue of an organic dye (b), hydrogen, halogen or C$_1$-C$_6$alkyl; C$_1$-C$_6$alkoxy; C$_1$-C$_6$alkylamino; C$_6$-C$_{10}$aryloxy; C$_6$-C$_{10}$arylamino; SO$_2$R$_1$; wherein at least one of Y$_1$ and Y$_2$ is a residue of an organic dye;

An$_1$ and An$_2$ independently from each other are an anion;

a and b independently from each other are a number from 1 to 3;

m is a number from 0 to 5000;

n is a number from 0 to 5000; and p is a number from 1 to 5000;

wherein the sum of m+n+p≧3.

5. Polymeric dye according to claim 4, wherein

X$_1$ and X$_2$, independently from each other are a bivalent radical of formula (2a) -(T)$_t$(Z)$_z$—, wherein T is a radical selected from saturated or unsaturated, linear or branched —C$_1$-C$_{12}$alkylene, —C(O)—, —(CH$_2$CH$_2$—O)$_{1-5}$—, —(CH$_2$CH$_2$CH$_2$—O)$_{1-5}$—, —C(O)O—, —OC(O)—, —N(R$_1$)—, —CON(R$_1$)—, —(R$_1$)NC(O)—, —O—, —S—, —S(O)—, —S(O)$_2$—, —S(O)$_2$—N(R$_1$)—, and —N$^+$(R$_1$)(R$_2$)—, which may be interrupted and/or terminated at one or both ends by one or more than one —O—, —S—, —SO$_2$—, —N(R$_5$)—, —C(O)—,

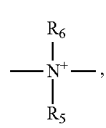

—CON(R$_5$)—, —(R$_5$)NC(O)— and which is optionally substituted by C$_1$-C$_6$alkyl, C$_1$-C$_6$alkoxy, C$_6$aryl, halogen, hydroxy or Y$^+$; or is a direct bond;

Z is —(CH$_2$)$_2$SO$_2$—; —CH$_2$CHRCO—NR$_1$—; or a biradical of formula

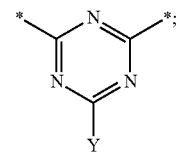

(3a)

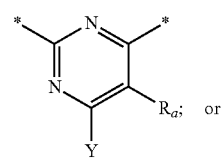

(3b)

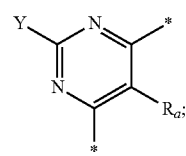

(3c)

R$_1$ and R$_2$ independently from each other are hydrogen; C$_1$-C$_6$alkyl; C$_1$-C$_6$alkoxy; C$_1$-C$_6$alkylamino; C$_6$-C$_{10}$aryloxy; or C$_6$-C$_{10}$arylamino;

R$_a$ is hydrogen; C$_1$-C$_6$alkyl; C$_1$-C$_6$-alkoxy; C$_1$-C$_6$-alkylamino; C$_6$-C$_{10}$-aryloxy; C$_6$-C$_{10}$-arylamino; SO$_2$R$_1$; chlorine; or fluorine;

Y is R$_a$; Y$_1^{a+}$; or Y$_2^{b+}$;

Y$_1^{a+}$ and Y$_2^{b+}$ are halogen; hydrogen; CH$_3$; or a residue of an organic dye selected from the group consisting of 1,4-diamino-anthraquinone, thiazolazo, benzothiazolazo, thiadiazolazo and imidazolazo dyes, wherein at least one of the Y$_1^{a+}$ and Y$_2^{b+}$ is a residue of an organic dye; and a and b independently from each other are 1, 2 or 3.

6. Dyes according to claim 5, wherein

T is selected from —C$_2$-C$_3$alkylene-; C(O)—; —C(O)—CH$_2$—; and —S(O)$_2$—C$_{2-6}$alkylene-;

Z is hydrogen or C$_1$-C$_6$ alkyl; or a a biradical of formula

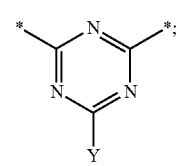

(3a)

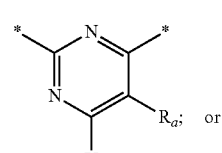

(3b)

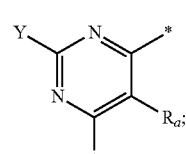

(3c)

R$_1$ and R$_2$ independently from each other are hydrogen; C$_1$-C$_3$alkyl; C$_1$-C$_4$-alkoxy; C$_1$-C$_4$-alkylamino; C$_6$aryloxy; or C$_6$arylamino;

$R_a$ is chlorine, fluorine, methyl or $SO_2CH_3$;

$Y_1^{a+}$ and $Y_2^{b+}$ are hydrogen; halogen; $CH_3$; or a residue of an organic dye selected from 1,4-diaminosubstituted anthraquinone, thiazolazo, benzothiazolazo, thiadiazolazo and imidazolazo dyes, wherein at least one of the $Y_1^{a+}$ and $Y_2^{b+}$ is a residue of an organic dye;

t and z, independently from each other are 0 or 1, with the proviso that at least one of t or z is 1.

7. Dye according to claim 1, wherein the molecular weight of the polymeric dye is from 400 to 500000.

8. Dye according to claim 1, wherein the polymer is a polyethyleneimine with a average molecular weight from 400-1800 g/mol, and the organic dye is bound via the primary secondary or tertiary amines of the polyethyleneimine.

9. Dye according to claim 1, wherein the polymer is a homopolymer or a copolymer of 4-vinylpyridine or 2-vinylpyridine or vinylimidazole.

10. Dye according to claim 1, which corresponds to formula

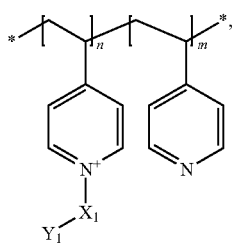

(3)

wherein the poly-4-vinylpyridine has an average molecular weight of MW=1000 and 500000 g/mol, $Y_1$ is a residue of an organic dye (b) as defined in claim 1, $X_1$ is defined as a linkage group selected from $—C_1-C_{30}$alkylene-, $—C_2-C_{12}$alkenylene-, $—C_5-C_{10}$arylene, $—C_5-C_{10}$cycloalkylene or $—C_1-C_{10}$alkylene($C_5-C_{10}$arylene) which may be interrupted and/or terminated at one or both ends by one or more than one —O—, —S—, —N=, $—N(R_1)$—, $S(O)$—, $—SO_2$—, $—(CH_2CH_2—O)_{1-5}$—, $—(CH_2CH_2CH_2—O)_{1-5}$—, —C(O)—, —C(O)O—, —OC(O)—,

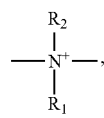

$—CON(R_1)$—, $—C(NR_1R_2)_2$—, $—(R_1)NC(O)$—, $—C(S)R_1$— or an optionally substituted, saturated or unsaturated, fused or non-fused aromatic or nonaromatic (hetero)cyclic bivalent radical optionally comprising at least one heteroatom; —O—; $—N(R_1)$—; —S(O)—; $SO_2$—; $—CH_2CH_2—O)_{1-5}$—; —C(O)—; —C(O)—, —OC(O)—;

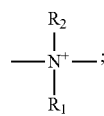

$—C(O)N(R_1)$—; $S(O)_2N(R_1)$—; $—C(NR_1R_2)_2$—; $—(R_1)NC(O)$—; $—C(S)R_1$—; saturated or unsaturated, fused or non-fused aromatic or nonaromatic bivalent radical optionally comprising at least one heteroatom, which is optionally substituted by $C_1-C_{30}$alkyl, $C_1-C_{30}$alkoxy, $C_2-C_{12}$alkenyl, $C_5-C_{10}$aryl, $C_5-C_{10}$cycloalkyl, $C_1-C_{10}$hydroxy($C_5-C_{10}$arylene), halogen, hydroxy; or the direct bond;

$R_1$ and $R_2$ independently from each other hydrogen; unsubstituted or substituted, straight-chain or branched, monocyclic or polycyclic, interrupted or uninterrupted $C_1-C_{14}$alkyl; $C_1-C_{14}$ hydroxyalkyl; $C_1-C_{14}$-aminoalkyl; $C_2-C_{14}$alkenyl; $C_6-C_{10}$aryl; $C_6-C_{10}$aryl-$C_1-C_{10}$alkyl; or $C_5-C_{10}$alkyl($C_5-C_{10}$aryl); and the ratio of n:m is between 1:10 and 10:1.

11. Dye according to claim 4, which corresponds to formula

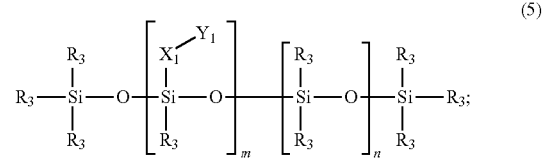

(5)

wherein $R_3$ is $C_1-C_5$alkyl.

12. Dye according to claim 4, which corresponds to formula

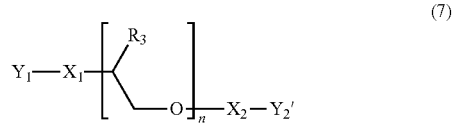

(7)

wherein $R_3$ is $C_1-C_5$alkyl.

13. Process for the preparation of the dyes according to claim 1 by using at least one of the following reactive dye building blocks

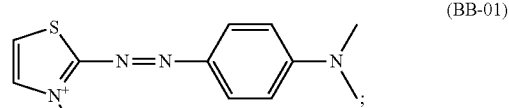

(BB-01)

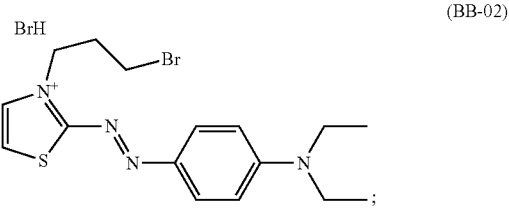

(BB-02)

(BB-03)
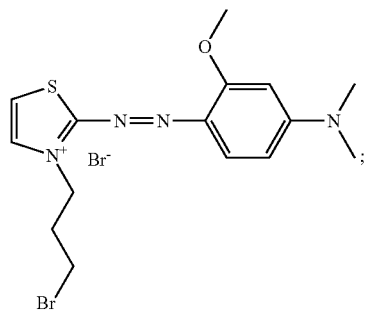
(BB-04)
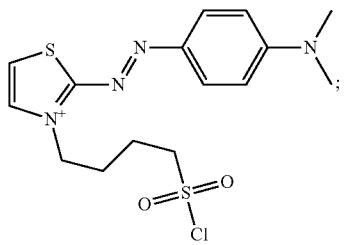
(BB-05)
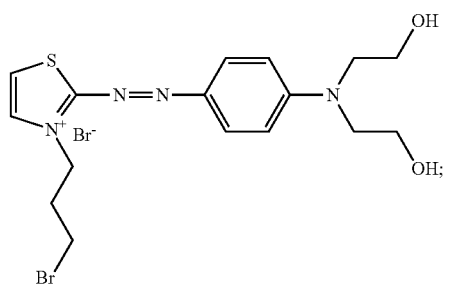
(BB-06)
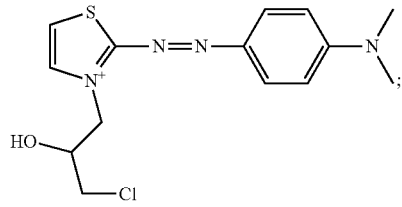
(BB-07)
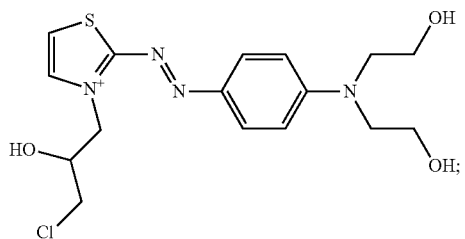
(BB-08)
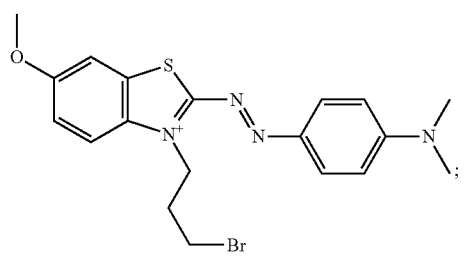
(BB-09)
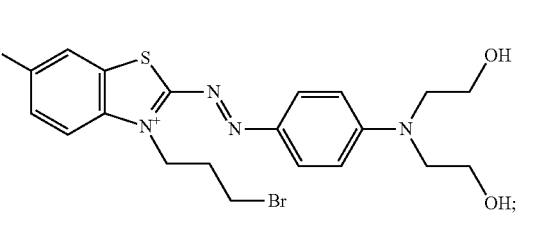
(BB-12)
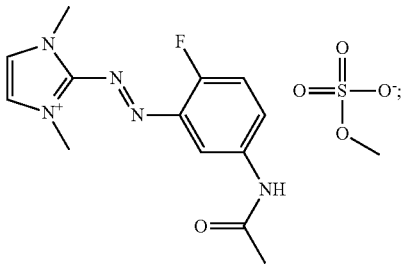
(BB-13)
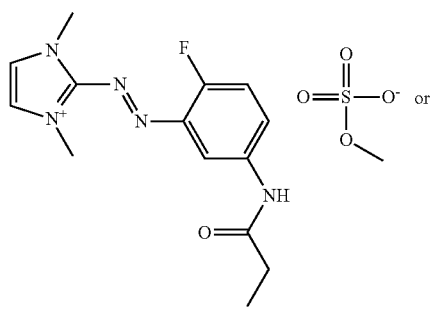
(BB-14)
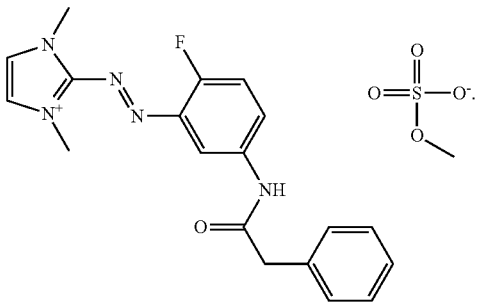
14. Dyes prepared by the reaction between polyethyleneimine and compounds of formula
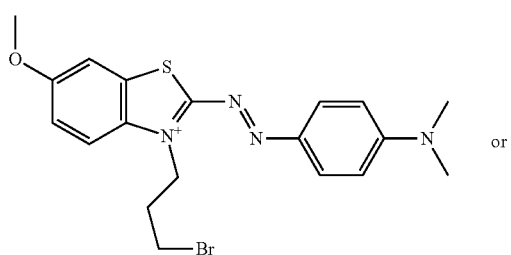

-continued

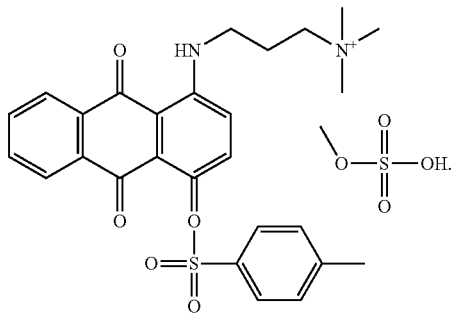

(10)

15. A composition comprising at least one dye of formula (1a) or (1b) as defined in claim 4.

16. A composition according to claim 15 comprising in addition at least one single further direct dye and/or an oxidative agent.

17. A composition according to claim 15 in form of a shampoo, a conditioner, a gel or an emulsion.

18. A method of dyeing organic material, which comprises treating the organic material with at least one dye of formula (1a), (1b) or (1c) according to claim 4.

19. A method according to claim 18, which comprises treating the organic material with at least one dye of formula (1a), (1b) or (1c) and an oxidative agent and, optionally, a further direct dye.

20. A method according to claim 18, which comprises treating the organic material with at least one compound of formula (1a), (1b) or (1c) and at least one single oxidative dye, or treating the organic material with a dye of formula (1a), (1b) or (1c) and at least one single oxidative dye and an oxidative agent.

21. A method according to claim 18 wherein the organic material is selected from keratin-containing fibers.

22. A method according to claim 21 wherein the keratin-containing fiber is human hair.

* * * * *